United States Patent [19]
Granoff et al.

[11] Patent Number: 6,030,619
[45] Date of Patent: Feb. 29, 2000

[54] MOLECULAR MIMETICS OF MENINGOCOCCAL B EPITOPES

[75] Inventors: Dan M. Granoff, Berkeley; Gregory R. Moe, Alameda, both of Calif.

[73] Assignee: Chiron Corporation, Emeryville, Calif.

[21] Appl. No.: 09/140,092

[22] Filed: Aug. 26, 1998

Related U.S. Application Data

[60] Provisional application No. 60/058,001, Aug. 27, 1997.

[51] Int. Cl.⁷ .......................... A61K 38/05; A61K 38/06; A61K 39/095; C07K 5/062; C07K 5/083
[52] U.S. Cl. ...................................... 424/185.1; 424/250.1; 424/257.1; 436/506; 436/811; 514/18; 514/19; 530/331; 548/159; 548/180; 548/217; 548/304.4; 548/306.1; 548/309.7; 548/458; 548/491; 564/153; 562/26; 562/433; 562/450
[58] Field of Search ........................... 424/185, 1, 193.1, 424/250.1, 257.1; 514/2, 18, 19; 530/300, 331; 548/159, 178, 180, 217, 304.4, 306.1, 309.7, 458, 491; 562/26, 433, 450; 564/153; 436/506, 518, 536, 86, 811

[56] References Cited

U.S. PATENT DOCUMENTS

| | | | |
|---|---|---|---|
| 4,727,136 | 2/1988 | Jennings | 530/395 |
| 5,475,106 | 12/1995 | Boorzat et al. | 544/58.4 |
| 5,556,757 | 9/1996 | Alstyne et al. | 435/7.2 |

FOREIGN PATENT DOCUMENTS

| | | |
|---|---|---|
| 0 109 688 | 5/1984 | European Pat. Off. . |
| 0 504 202 B1 | 5/1995 | European Pat. Off. . |
| WO 92/16232 | 10/1992 | WIPO . |
| WO 96/40202 | 12/1996 | WIPO . |
| WO 97/46582 | 12/1997 | WIPO . |

OTHER PUBLICATIONS

Figliozzi et al., "Synthesis of N–Substituted Glycine Peptoid Libraries," *Methods in Enzymology* 267:437–447(1996).

Granoff et al., "Antibody Responses to the Capsular Polysaccharide of *Neisseria meningitidis* Serogroup B in Patients with Meningococcal Disease," *Clinical and Diagnostic Laboratory Immunology* 2(5):574–582 (1995).

Granoff et al., "Bactericidal Monoclonal Antibodies That Define Unique Meningococcal B Polysaccharide Epitopes That Do Not Cross–React with Human Polysialic Acid," *The Journal of Immunology* 160:5028–5036 (1998).

Jennings et al., "Induction of *Meningococcal* Group B Polysaccharide–Specific IgG Antibodies in Mice by Using an N–Propionylated B Polysaccharide–Tetanus Toxoid Conjugate Vaccine," *The J. Of Immunology* 137(5):1708–1713(1986).

Jennings et al., "N–Propionylated Group B Meningococcal Polysaccharide Mimics a Unique Epitope on Group B *Neisseria Meningitidis*," *J. Experimental Medicine* 165:1207–1211 (1987).

Westerink et al., "Development and Characterization of an Anti–Idiotype Antibody to the Capsular Polysaccharide of *Neisseria Mengingitidis* Serogroup C," *Infection and Immunity* 56(5):1120–1127 (1988).

Westerlink et al., "Peptide Mimicry of the Menigococcal Group C Capsular Polyasccharide," *Proc. Nat. Acad. Sci. USA* 92:4021–4025 (1995).

Zuckermann et al., "Design, Construction and Application of a Fully Automated Equimolar Peptide Mixture Synthesizer," *Pept. Protein Res.* 40:498 (1992).

Chemical Abstract 113:231990r, p. 784, 1990.

Zuckermann et al, Discovery of Nanomolar Ligands . . . J. Med. Chem. vol. 37, pp. 2678–2685, 1994.

*Primary Examiner*—Jeffrey E. Russel
*Attorney, Agent, or Firm*—Roberta L. Robins; Alisa A. Harbin; Robert P. Blackburn

[57] ABSTRACT

Molecular mimetics of unique epitopes of *Neisseria meningitidis* serogroup B ("MenB") are disclosed. Compositions containing such molecular mimetics can be used to prevent MenB or *E. coli* K1 disease without the risk of evoking autoantibody responses.

19 Claims, 3 Drawing Sheets

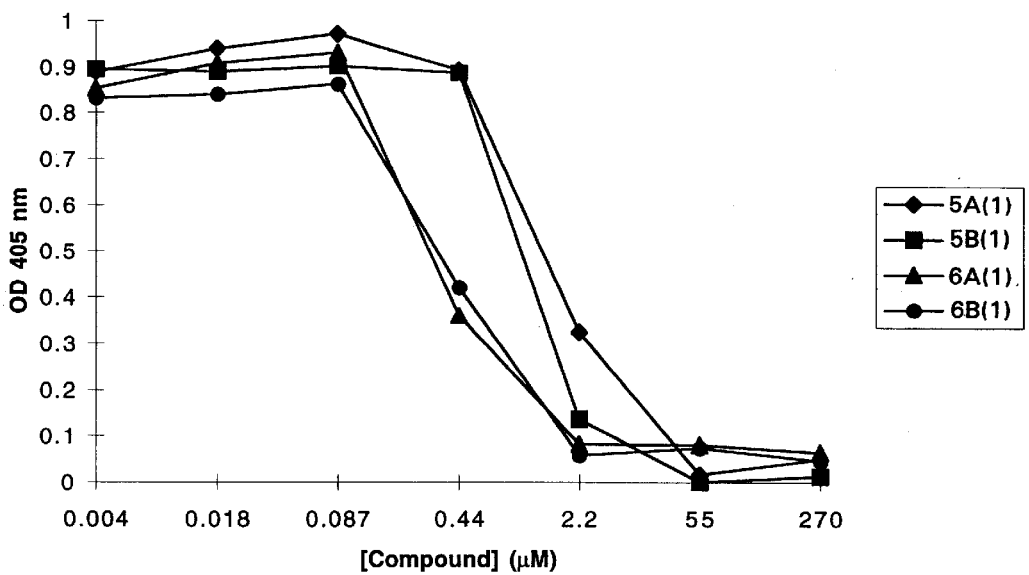
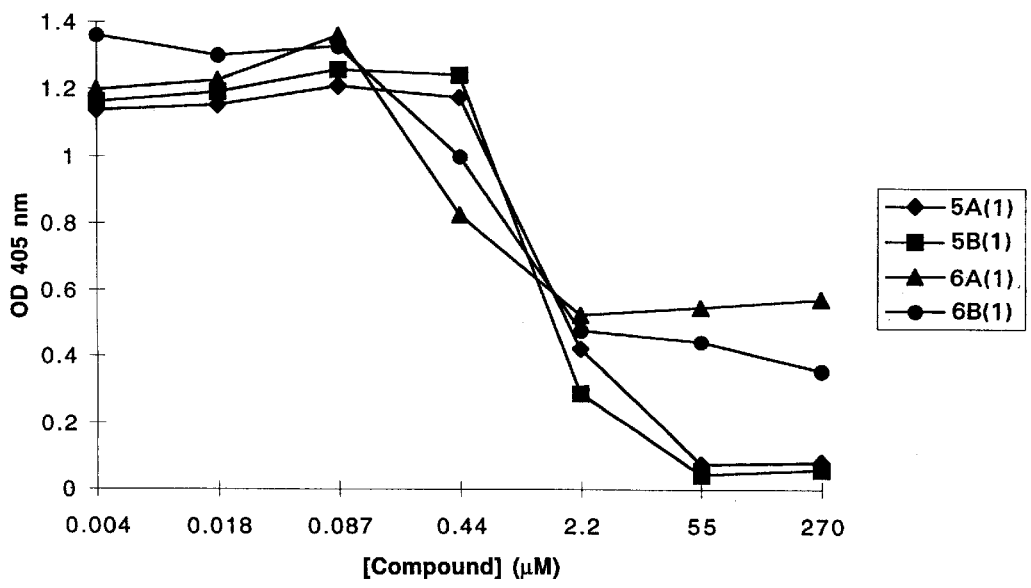

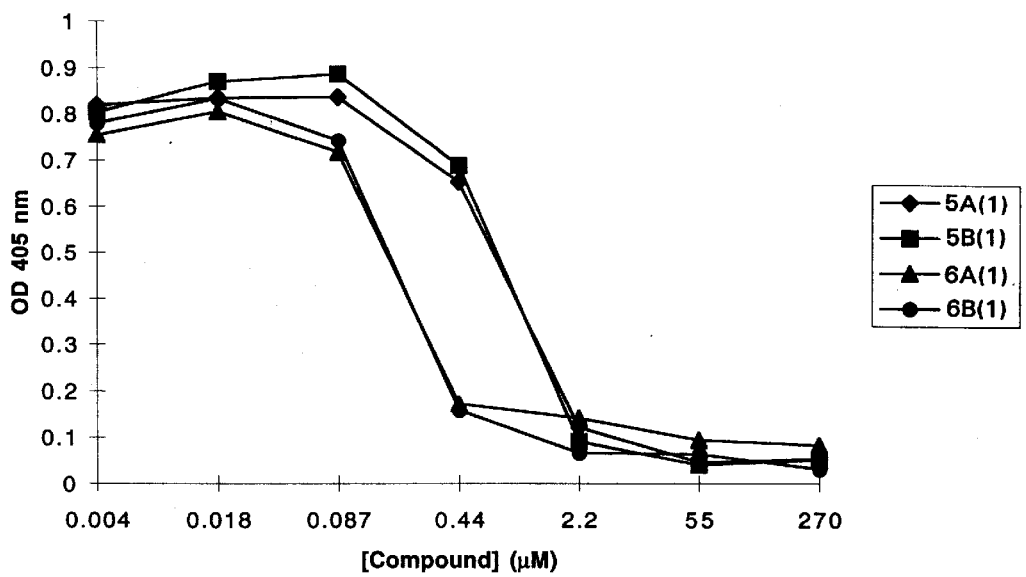
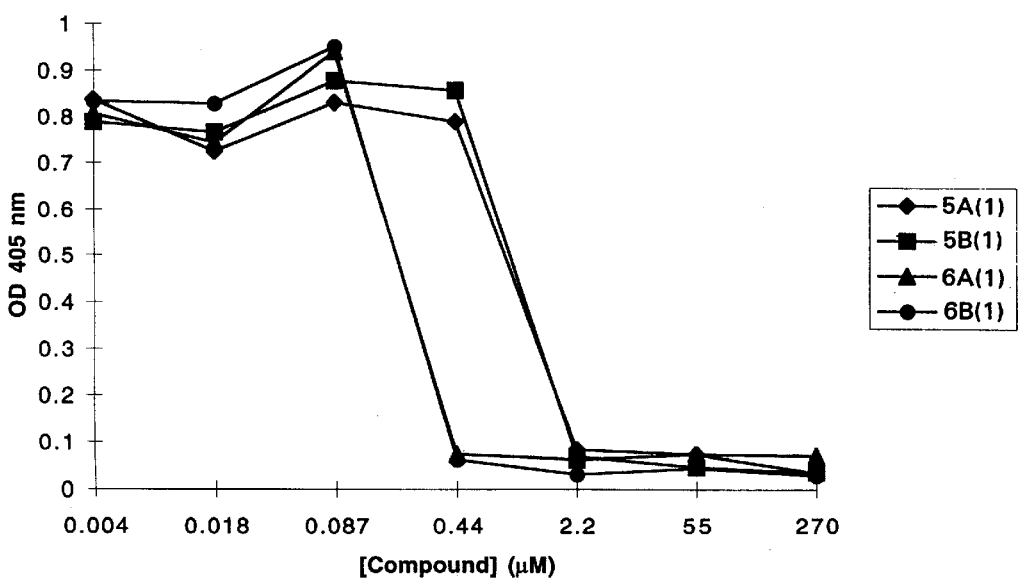

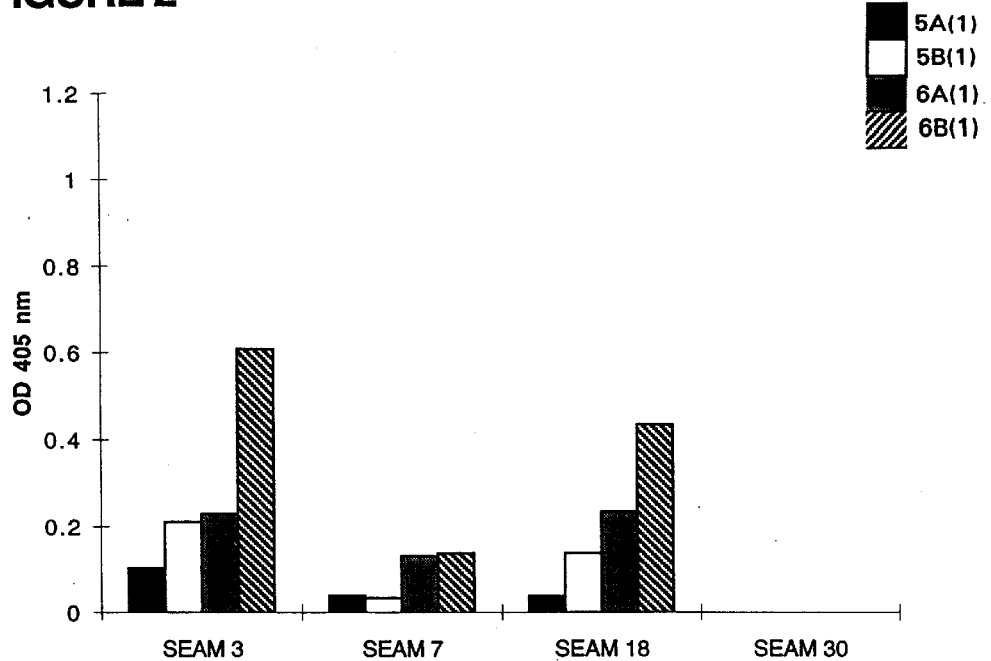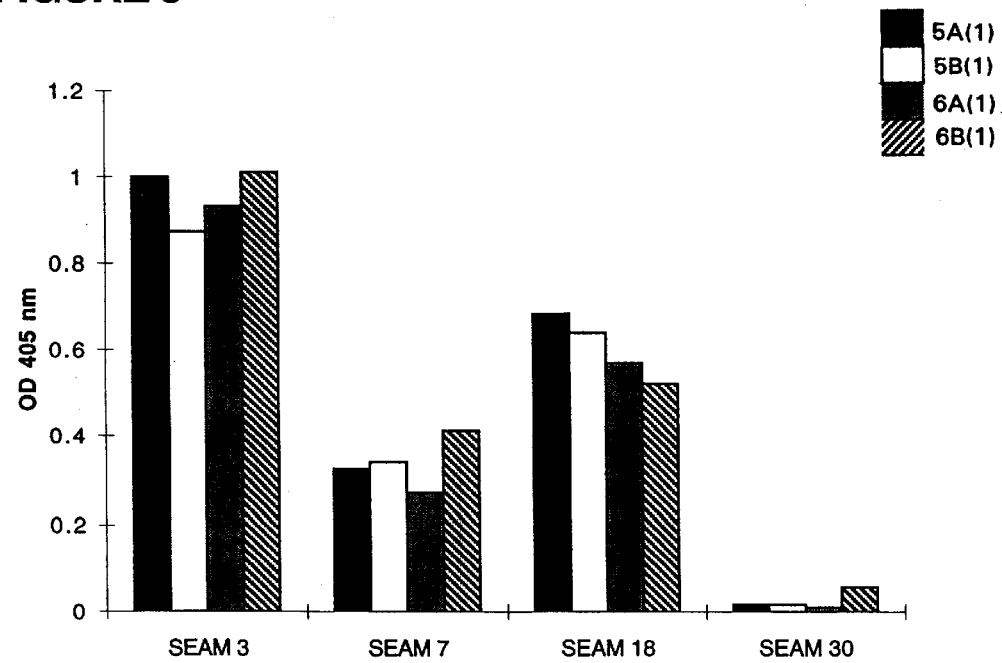

MOLECULAR MIMETICS OF MENINGOCOCCAL B EPITOPES

CROSS-REFERENCE TO RELATED APPLICATION

This application is related to provisional patent applications serial no. 60/058,001, filed Aug. 27, 1997 from which priority is claimed under 35 USC §119(e)(1) and which application is incorporated herein by reference in its entirety.

TECHNICAL FIELD

The present invention pertains generally to bacterial pathogens. In particular, the invention relates to molecular mimetics of *Neisseria meningitidis* serogroup B (MenB) epitopes identified using anti-MenB antibodies that lack autoimmune activity.

BACKGROUND OF THE INVENTION

*Neisseria meningitidis* is a causative agent of bacterial meningitis and sepsis. Meningococci are divided into serological groups based on the immunological characteristics of capsular and cell wall antigens. Currently recognized serogroups include A, B, C, D, W-135, X, Y, Z and 29E. The polysaccharides responsible for the serogroup specificity have been purified from several of these groups, including A, B, C, D, W-135 and Y.

*N. meningilidis* serogroup B ("MenB") accounts for approximately 50 percent of bacterial meningitis in infants and children residing in the U.S. and Europe. The organism also causes fatal sepsis in young adults. In adolescents, experimental MenB vaccines consisting of outer membrane protein (OMP) vesicles have been found to be approximately 50% protective. However, no protection has been observed in vaccinated infants and children, the age groups at greatest risk of disease. Additionally, OMP vaccines are serotype- and subtype-specific, and the dominant MenB strains are subject to both geographic and temporal variation, limiting the usefulness of such vaccines.

Effective capsular polysaccharide-based vaccines have been developed against meningococcal disease caused by serogroups A, C, Y and W135. However, similar attempts to develop a MenB polysaccharide vaccine have failed due to the poor immunogenicity of the capsular MenB polysaccharide (termed "MenB PS" herein). MenB PS is a homopolymer of (N-acetyl ($\alpha$ 2→8) neuraminic acid. *Escherichia coli* K1 has the identical capsular polysaccharide. Antibodies elicited by MenB PS cross-react with host polysialic acid (PSA). PSA is abundantly expressed in fetal and newborn tissue, especially on neural cell adhesion molecules ("NCAMs") found in brain tissue. PSA is also found to a lesser extent in adult tissues including in kidney, heart and the olfactory nerve. Thus, most anti-MenB PS antibodies are also autoantibodies. Such antibodies therefore have the potential to adversely affect fetal development, or to lead to autoimmune disease.

MenB PS derivatives have been prepared in an attempt to circumvent the poor immunogenicity of MenB PS. For example, $C_3$–$C_8$ N-acyl-substituted MenB PS derivatives have been described. See, EP Publication No. 504,202 B, to Jennings et al. Similarly, U.S. Pat. No. 4,727,136 to Jennings et al. describes an N-propionylated MenB PS molecule, termed "NPr-MenB PS" herein. Mice immunized with NPr-MenB PS glycoconjugates were reported to elicit high titers of IgG antibodies. Jennings et al. (1986) *J. Immunol.* 137:1708. In rabbits, two distinct populations of antibodies, purportedly associated with two different epitopes, one shared by native MenB PS and one unshared, were produced using the derivative. Bactericidal activity was found in the antibody population that did not cross react with MenB PS. Jennings et al. (1987) *J. Exp. Med.* 165:1207. The identity of the bacterial surface epitope(s) reacting with the protective antibodies elicited by this conjugate remains unknown.

Peptides can serve as mimics of polysaccharides by binding to polysaccharide-specific antibodies as well as to other polysaccharide binding proteins. For example, concanavalin A (Con A), which binds to oligosaccharides bearing terminal alpha-linked mannose or glucose residues, has been used to select peptide mimetics from random libraries of bacterial phage bearing short peptide sequences at the amino-terminus of the pIII coat protein. Oldenberg et al. (1992) *Proc. Natl. Acad. Sci. USA* 89:5393; Scott et al. (1992) *Proc. Natl. Acad. Sci. USA* 89:5398. Similarly, monoclonal antibodies have identified peptide mimetics of a carbohydrate present on the surface of adenocarcinoma cells from a phage library. Hoess et al. (1993) *Gene* 128:43.

Peptides can also elicit polysaccharide-specific antibodies. For example, Westerink et al. (1988) *Infect. Immun.* 56:1120, used a monoclonal antibody to the *N. meningitidis* serogroup C ("MenC") capsular polysaccharide to elicit an anti-idiotype antibody. Mice immunized with the anti-idiotype antibody were protected against infection with a lethal dose of MenC bacteria. These experimenters subsequently demonstrated that a peptide fragment of a MenC anti-idiotype antibody elicited serum anti-MenC antibodies and protected animals from bacteremia and death after lethal challenge with MenC bacteria. Westerink et al. (1995) *Proc. Natl. Acad. Sci. USA* 92:4021.

However, to date, no such approach has been taken with respect to MenB vaccine development. It is readily apparent that the production of a safe and effective vaccine against MenB would be particularly desirable.

SUMMARY OF THE INVENTION

In commonly owned U.S. patent application, Ser. No. 08/925,002 filed on Aug. 27, 1997, which application is incorporated herein by reference in its entirety, a number of functionally active antibodies directed against MenB PS derivatives are described. These antibodies do not cross-react, or are minimally cross-reactive, with host tissues, and thus pose minimal risk of evoking autoimmune disease and are termed "non-autoreactive" herein. These non-autoreactive antibodies are used herein to identify molecular mimetics of unique MenB PS epitopes that can be used in vaccine compositions.

Accordingly, in one embodiment, the subject invention relates to molecular mimetics of unique epitopes of MenB PS. These molecular mimetics are comprised of novel compounds, identified using functionally active antibodies directed against MenB PS derivatives that do not cross-react, or are minimally cross-reactive, with host tissue. Such novel molecular mimetics are represented by the following structure 1:

(1)

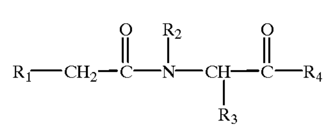

wherein:

$R_1$ is —$NR_5R_6$ $R_2$ is —$(CH_2)_p$—$R_{11}$, wherein p is an integer from 0–8;

$R_3$ H, 1–6C alkyl, aryl, alkyl-aryl, 2–6C alkenyl, or 2–6C alkynyl;

$R_4$ is —$NH_2$, —NHOH, —$NHNH_2$, —OH, —SH, or a multivalent linker moiety selected from the group of amines such as —$NH(CH_2)_qSH$, amino acids, peptoids and peptides, wherein q is an integer from 1–5;

$R_5$ is $R_2$, H or $R_5$ and $R_6$ taken together form a carbocyclic or aryl ring, said ring optionally containing up to two heteroatoms consisting of N, 0 and S;

$R_6$ is —CO—$(CH_2)_m$—$R_7$, wherein m is an integer from 1–6;

$R_7 = $ —N($R_8$)—$(CH_2)_n$—$R_9$ or —C$_6$H$_4$—$R_{10}$ wherein n is an integer from 0–5;

$R_8$ is H, 1–3C alkyl or acyl;

$R_9$ is —$NH_2$, —NH—$NH_2$, —$CONH_2$, acyl, —COOH, —SH; —S-alkyl, —S-aryl, sulfonic acid or sulfonamide, with the proviso that when n=0, $R_9$ is not —NH—$NH_2$;

$R_{10}$ is H, 1–6C alkyl, halogen, OH, 1–6C alkoxy, acyl, amino, 1–5C alkylamino, amide, —COOH, —SH, —S-alkyl, —S-aryl, sulfonic acid or sulfonamide; and $R_{11}$ is a carbocyclic ring or an aryl, which is optionally substituted, —CH=CH—$(CH_2)_p$—$CH_3$, —$CF_3$, —OH, 1–6C alkoxy, acyl, amino, —$N(CH_3)_2$, —NH—$NH_2$, amide, —COOH, —SH; —S-alkyl, —S-aryl, sulfonic acid or sulfonamide.

In preferred embodiments, the molecular mimetic is represented by the following structures:

(2)

wherein X is O, N, S or $CH_2$; $R_3$ is H or alkyl; $R_4$ is —$NH_2$, —NHOH, —$NHNH_2$, —OH or —SH, and p=0–3;

(3)

wherein X is O, N, S or $CH_2$; $R_3$ is H or alkyl; $R_4$ is —$NH_2$, —NHOH, —$NHNH_2$, —OH or —SH, and p=0–3;

(4)

wherein X is O, N, S or $CH_2$; $R_3$ is H or alkyl; $R_4$ is —$NH_2$, —NHOH, —$NHNH_2$, —OH or —SH, and p=0–3;

(5A)

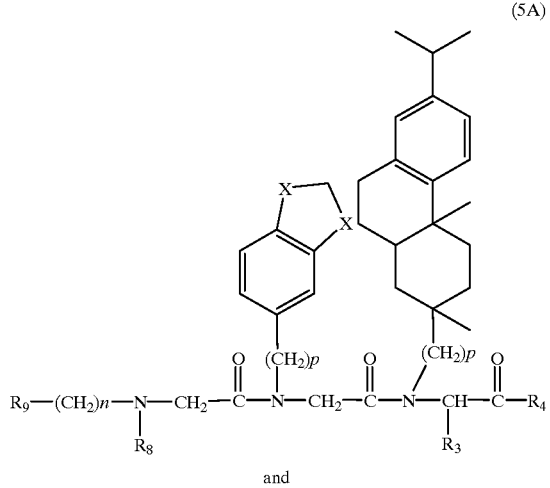

and (5B)

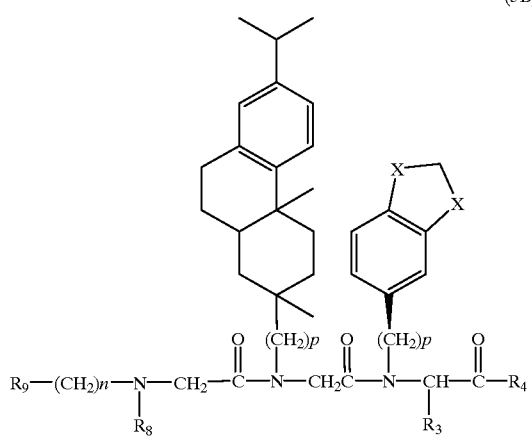

wherein X is O, N, S or CH$_2$; R$_3$ is H or alkyl; R$_4$ is —NH$_2$, —NHOH, —NHNH$_2$, —OH or —SH; R$_8$ is H or COCH$_3$; p=0–3; and R$_9$ is —COOH, —NH$_2$, —NHNH$_2$ or

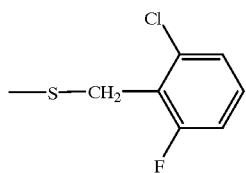

(6A)

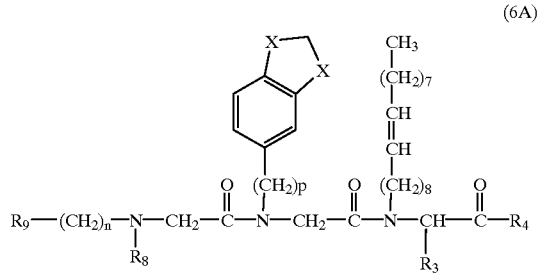

and (6B)

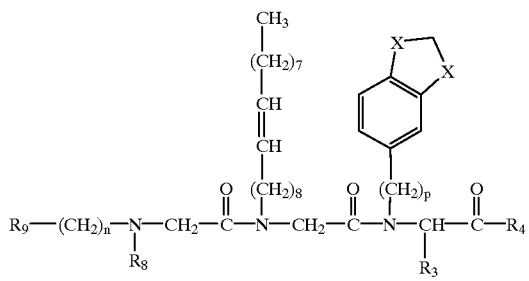

wherein X is O, N, S or CH$_2$; R$_3$ is H or alkyl; R$_4$ is —NH$_2$, —NHOH, —NHNH$_2$, —OH or —SH; R$_8$ is H or COCH$_3$; p=0–3; and R$_9$ is —COOH, —NH$_2$, —NHNH$_2$ or

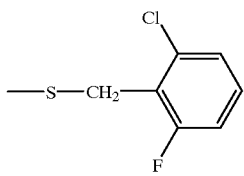

In another embodiment, the invention is directed to a composition, comprising a molecular mimetic of a unique epitope of MenB, as described above, in combination with a pharmaceutically acceptable excipient.

In another embodiment, the subject invention is directed to a method for preventing MenB and/or E. coli K1 disease in a mammalian subject comprising administering an effective amount of the above composition to the subject.

In another embodiment, the invention is directed to a method for isolating a molecular mimetic of a unique epitope of Neisseria meningitidis serogroup B (MenB), said method comprising:

(a) providing a population of molecules comprising a putative molecular mimetic of a unique epitope of MenB;

(b) contacting said population with an antibody directed against a Neisseria meningitidis serogroup B capsular polysaccharide (MenB PS) in an ELISA and is not autoreactive, wherein the contacting is carried out under conditions that allow immunological binding between the antibody and the above described molecule, if present, to provide a complex; and (c) separating the complexes form the non-bound molecules.

In another embodiment, the invention is directed to a method for detecting *Neisseria meningitidis* serogroup B and/or *E. coli* K1 antibodies in a biological sample comprising:

(a) providing a biological sample;

(b) reacting said biological sample with a molecular mimetic of the invention under conditions which allow *Neisseria meningitidis* serogroup B and/or *E. coli* K1 antibodies, when present in the biological sample, to bind to the molecular mimetic to form an antibody/mimetic complex; and (c) detecting the presence or absence of the complex thereby detecting the presence or absence of *Neisseria meningitidis* serogroup B and/or *E. coli* K1 antibodies in the sample.

These and other embodiments of the present invention will readily occur to those of ordinary skill in the art in view of the disclosure herein.

BRIEF DESCRIPTION OF THE FIGURES

FIGS. 1A–1D depict the concentration-dependent inhibition of (A) SEAM 3 (10 μg/ml), (B) SEAM 7 (10 μg/ml), (C) SEAM 18 (10 μg/ml), (D) SEAM 30 (10 μg/ml) binding to NPr-MenB PS by structure 5A(1) (filled diamond), structure 5B(1) (filled square), structure 6A(1) (filled triangle), and structure 6B(1) (filled circle) in an ELISA format.

FIG. 2 depicts the binding of SEAM 3 (10 μg/ml), SEAM 7 (10 μg/ml), SEAM 18 (10 μg/ml), and SEAM 30 (10 μg/ml) to structure 5A(1) (filled bars), structure 5B(1) (open bars), structure 6A(1) (shaded bars), and structure 6B(1) (cross-hatched bars) in an ELISA format.

FIG. 3 depicts the cross-reactivity of SEAM antibodies with BSA conjugates of structures 5A(1), 5B(1), 6A(1) and 6B(1). Particularly, FIG. 3 depicts the binding of SEAM 3 (10 mg/ml), SEAM 7 (10 mg/ml), SEAM 18 (10 mg/ml) and SEAM 30 (10 mg/ml) to 5A(1) (filled bars), structure 5B(1) (open bars), structure 6A(1) (shaded bars), and structure 6B(1) (cross-hatched bars).

DETAILED DESCRIPTION OF THE INVENTION

The practice of the present invention will employ, unless otherwise indicated, conventional methods of immunology, microbiology, and molecular biology within the skill of the art. Such techniques are explained fully in the literature. See, e.g., Sambrook, et al. *Molecular Cloning: A Laboratory Manual* (2nd Edition, 1989); Morrison and Boyd, *Organic Chemistry* (3rd Edition 1973); Carey and Sundberg, *Advanced Organic Chemistry* (2nd Edition, 1985); Smith, M. B., *Organic Synthesis* (1994); Perbal, *A Practical Guide to Molecular Cloning* (1984); and *Handbook of Experimental Immunology*, Vols. I–IV (D. M. Weir and C. C. Blackwell eds., 1986, Blackwesll Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

As used herein, a "MenB PS derivative" refers to a molecule obtained by the chemical modification of the native capsular polysaccharide of MenB. Such MenB PS derivatives include, but are not limited to, MenB PS molecules which have been modified by the substitution of sialic acid residue N-acetyl groups of the native molecule with appropriate acyl groups, such as $C_3$–$C_8$, and higher, acyl groups wherein the term "acyl group" encompasses any acylated linear, branched, aliphatic or aromatic molecule. A particularly preferred MenB PS derivative for use herein comprises the substitution of N-propionyl groups for N-acetyl groups of native MenB PS (termed "NPr-MenB PS" herein). Methods for synthesizing N-acyl-substituted MenB PS derivatives, including NPr-MenB PS, are known in the art and described in e.g., U.S. Pat. No. 4,727,136 to Jennings et al. and EP Publication No. 504,202 B, also to Jennings et al.

"Molecular mimetics" of MenB PS, or derivatives of MenB PS are molecules that functionally mimic at least one "unique" epitope expressed on a MenB bacteria. A "unique epitope" is an epitope capable of eliciting the formation of functionally active (e.g., opsonic and/or complement-mediated bactericidal) anti-MenB antibodies that either are not cross-reactive with polysialic acid in host tissue and hence lack autoimmune activity, or are minimally cross-reactive. Such molecular mimetics are useful in vaccine compositions and in eliciting antibodies for diagnostic or therapeutic applications, as described further below. Molecular mimetics include, but are not limited to: small organic compounds; nucleic acids and nucleic acid derivatives; saccharides or oligosaccharides; peptide mimetics including peptides, proteins, and derivatives thereof, such as peptides containing non-peptide organic moieties, synthetic peptides which may or may not contain amino acids and/or peptide bonds, but retain the structural and functional features of a peptide ligand; pyrrolidines; peptoids and oligopeptoids which are molecules comprising N-substituted glycine, such as those described by Simon et al. (1992) *Proc. Natl. Acad. Sci. USA* 89:9367; and antibodies, including anti-idiotype antibodies. Methods for the identification and production of molecular mimetics are described more fully below.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Preferred alkyl groups herein contain 1 to 12 carbon atoms, and the most preferred alkyl groups herein contain one to six carbon atoms. Further, these groups are optionally substituted with one or more, alkoxy, hydroxyl, amino, amide, halogen, nitro, acyl, carboxyl, thiol, sulfonic acids, sulfonamide, and the like.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, t-butenyl, octenyl, decenyl, tetradecenyl, hexadecenyl, eicosenyl, tetracosenyl, as well as cyclic alkenyl group of three to eight, preferably five or six, carbon atoms, and the like. Preferred alkenyl groups herein contain 2 to 12 carbon atoms, more preferably two to six carbon atoms. Further, these groups are optionally substituted with one or more, alkyl, alkoxy, hydroxyl, amino, amide, halogen, nitro, acyl, carboxyl, thiol, sulfonic acids, sulfonamide, and the like.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, t-butynyl, octynyl, decynyl and the like. Preferred alkynyl groups herein contain 2 to 12 carbon atoms, preferably two to six carbon atoms. Further, these groups are optionally substituted as described above.

The term "aryl" as used herein refers to a mono-, bi-, tri- and tetra-cyclic aromatic species containing five-, six- or seven-membered rings optionally containing one or more heteroatoms such as N, O, and S. Examples include but are not limited to phenyl, benzyl, naphthyl, pyrrole, furan, thiophene, imidazole, oxazole, thiazole, pyrazole, pyridine, pyrimidine, purine, quinoline, isoquinoline, carbazole, phenanthrene, anthracene, benzopyrene, azulene, indole, indane, and the like. Further, these groups are optionally substituted as described above.

The term "alkyl-aryl" as used herein refers to an aryl ring attached to an alkyl, wherein the terms alkyl and aryl are as defined above.

The term "carbocyclic ring" as used herein includes cylco-alkyl, -alkenyl, and -alkynyl, as described above, optionally containing one or more heteroatoms such as N, O, and S. Further, these groups are optionally substituted as described above.

The term "alkoxy" as used herein intends an alkyl group bound through a single, terminal ether linkage; that is, an "alkoxy" group may be defined as -OR where R is alkyl as defined above. In a preferred embodiment, an alkoxy group contains one to six, more preferably one to four, carbon atoms.

The term "acyl" is used in its conventional sense to refer to a molecular substituent RCO— where R is alkyl as defined above. In a preferred embodiment, an acyl group contains alkyl containing one to six, more preferably one to four, carbon atoms.

The term "peptoid" as used herein encompasses oligomers of N-substituted glycine and is used interchangeably with the term oligomeric N-substituted glycines (NSG).

The term "multivalent linker moiety" represents any suitable linker which may be attached to any suitable or attachable moiety, including a ceramide or a protein or a peptide, including a multiple antigen peptide, and is preferably a group with a reactive group thereon which covalently allows it to bind to other molecules, such as molecular mimetics and the like.

The term "antibody" encompasses polyclonal and monoclonal antibody preparations, as well as preparations including hybrid antibodies, altered antibodies, F(ab')$_2$ fragments, F(ab) molecules, Fv fragments, single chain fragment variable displayed on phage (scFv), single domain antibodies, chimeric antibodies and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, F(ab')$_2$ fragments, Fv fragments, single chain fragment variable displayed on phage (scFv), and other molecules that exhibit immunological binding properties of the parent monoclonal antibody molecule. Methods of making polyclonal and monoclonal antibodies are known in the art and described more fully below.

An "antigen" is defined herein to include any substance that may be specifically bound by an antibody molecule. An "immunogen" is an antigen that is capable of initiating lymphocyte activation resulting in an antigen-specific immune response.

By "epitope" is meant a site on an antigen to which specific B cells and T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments the polymer that are discontinuous in the linear sequence but are continuous in the folded conformation(s). Epitopes that are composed of single segments of biopolymers or other molecules are termed continuous or linear epitopes. T cell epitopes are generally restricted to linear peptides. A peptide epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance spectroscopy. Furthermore, the identification of epitopes in a given protein is readily accomplished using techniques well known in the art. See, e.g., Geysen et al. (1984) *Proc. Natl. Acad. Sci. USA* 81:3998 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709 (technique for identifying peptides with high affinity for a given antibody). Antibodies that recognize the same epitope can be identified in a simple immunoassay showing the ability of one antibody to block the binding of another antibody to a target antigen.

A "unique MenB epitope" is defined herein as an epitope present on a MenB bacterium, wherein antibodies directed toward the epitope are capable of binding specifically to MenB and not cross-reacting, or minimally cross-reacting, with sialic acid residues present on the surface of host tissue. Immunogens containing or mimicking one or more "unique MenB epitopes" are thus useful in vaccines for prevention of MenB disease, and will not elicit an autoimmune response, or pose minimal risk of eliciting an autoimmune response.

An antibody displays "functional activity" against a MenB organism when the antibody molecule exhibits complement-mediated bactericidal activity and/or opsonic activity against MenB as determined using the assays described herein.

An antibody specific for a "unique" MenB epitope "lacks autoimmune activity," and/or is "not autoreactive" when the subject antibody does not exhibit cross-reactive immunological binding properties with polysialic acid in host tissue as determined using the binding assays described herein.

An antibody specific for a "unique" MenB epitope exhibits "minimal autoreactivity," and/or is "minimally autoreactive" when the subject antibody requires approximately ten times greater antibody concentration to exhibit binding to polysialic acid in host tissues, compared to a known cross-reactive auto antibody considered positive in the binding assays described herein.

As used herein, the terms "immunological binding," and "immunological binding properties" refer to non-covalent interactions of the type which occur between an immunoglobulin molecule and an antigen for which the immunoglobulin is specific.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

II Modes of Carrying Out the Invention

The present invention is based on the discovery of molecular mimetics of unique epitopes of *Neisseria meningitidis* serogroup B (MenB), identified using functional antibodies directed against MenB. The antibodies do not cross-react, or are minimally cross-reactive with polysialic acid in host tissue, and hence the antibodies have a lower risk of evoking autoimmune activity than antibodies that are highly cross-reactive with host tissue. The mimetics can be used as diagnostic reagents and/or in compositions to prevent MenB and *E. coli* K1 disease.

As explained above, the native capsular polysaccharide of MenB, termed "MenB PS" herein, is poorly immunogenic in humans and other mammalian subjects. Furthermore, native MenB PS can elicit the production of autoantibodies and, hence, may be inappropriate for use in vaccine compositions. Thus, the present invention uses antibodies prepared against MenB PS derivatives. These antibodies were selected based on their ability to exhibit functional activity against MenB bacteria, wherein the functional activity is important in conferring protection against MenB disease. The antibodies were also selected on the basis of showing minimal or undetectable autoimmune activity.

More particularly, MenB PS derivatives were prepared for obtaining antibody molecules used to identify the molecular mimetics of the present invention. The derivatives generally comprise $C_3$–$C_8$ acyl substitutions of sialic acid residue N-acetyl groups of the native molecule. Particularly preferred MenB PS derivatives comprise the substitution of N-propionyl groups for N-acetyl groups of native MenB PS and are termed "NPr-MenB PS" herein. Such derivatives and methods for synthesizing the same are described in e.g., U.S. Pat. No. 4,727,136 and EP Publication No. 504,202 B, both to Jennings et al.

The $C_3$–$C_8$ acyl derivatives can be made by first treating native MenB (obtained from e.g., *N. meningitidis* cultures) in the presence of a strong base to quantitatively remove the N-acetyl groups and to provide a reactive amine group in the sialic acid residue parts of the molecule. The deacylated MenB PS fragments are then N-acylated. For example, in the case of NPr-MenB PS, the deacylated molecule is N-propionylated using a source of propionyl groups such as propionic anhydride or propionyl chloride, as described in U.S. Pat. No. 4,727,136 to Jennings et al. The extent of N-acylation can be determined using, for example, NMR spectroscopy. In general, reaction conditions are selected such that the extent of N-acylation is at least about 80%.

In order to increase the immunogenicity of the MenB PS derivatives, the derivatives can be conjugated to a suitable carrier molecule to provide glycoconjugates. Particularly, N-acylated MenB PS glycoconjugate preparations having well defined and controlled structural configurations can be formed from intermediate sized N-acylated MenB oligosaccharides as described below.

Thus, a group of N-acylated MenB PS glycoconjugates, an example of which is termed "CONJ-2" herein, can be prepared as follows. An N-acylated MenB PS preparation, having substantially 100% N-acylated sialic acid residues, as determined by, e.g., NMR analysis, can be fragmented under mild acidic conditions to provide a population of oligosaccharide molecules of varying sizes. The fragmented products are size fractionated, using for example, standard ion exchange chromatographic techniques combined with e.g., stepwise salt gradients, to provide fractions of N-acylated MenB molecules of homogenous sizes. Fractions containing intermediate sized oligosaccharides e.g., with an average Dp of about 5 to about 22, preferably 10 to about 20, and more particularly about 12 to about 18, are chemically end-activated at the non-reducing termini and conjugated to protein carriers by a reductive amination technique to provide the CONJ-2 glycoconjugates. Successful conjugation can be determined by, e.g., gel filtration, and the final saccharide to protein ratio (w/w) assessed by colorimetric assay.

Glycoconjugates formed from MenB PS derivatives, such as the CONJ-2, are then used herein to elicit the formation of anti-saccharide antibodies in an immunized host. A subset of such antibodies should bind to MenB bacteria, should not cross-react, or be minimally cross-reactive with host tissue sialic acid residues as determined using the binding assays described herein. The antibodies can be fully characterized with respect to isotype, fine antigenic specificity, functional activity and cross-reactivity with host tissue.

For example, mammalian subjects, conveniently, standard laboratory animals such as rodents and rabbits, can be immunized with compositions containing the glycoconjugates along with a suitable adjuvant to elicit the production of polyclonal sera. Groups of animals are generally immunized and boosted several times with the compositions. Antisera from immunized animals can be obtained, and polyclonal sera that does not cross-react with host tissue can be obtained using in-situ absorption or conventional affinity chromatography techniques. Successful glycoconjugate antigens can be identified by their ability to elicit a substantial IgG anti-MenB PS derivative antibody response, characteristic of a T-cell dependent antigen. Conjugates that are found to be highly immunogenic and produce predominantly IgG antibodies are particularly preferred for use in the methods of the present invention.

MenB PS derivatives that are capable of eliciting the formation of bactericidal antisera are suitable for use in the production of monoclonal antibodies. More particularly, the process used to provide the various MenB PS derivative conjugates is designed to produce superior immunogens presenting unique saccharide-associated epitopes that mimic those found on the surface of MenB organisms and are expressed minimally in the host. The MenB PS derivatives described herein are thus capable of eliciting the production of MenB-specific antibodies that are used to search for mimetics of MenB polysaccharide antigens that will provide unique epitopes for anti-MenB vaccines.

Thus, in the practice of the invention, selected MenB derivatives are used to provide monoclonal antibodies and functional equivalents thereof. The term "functional equivalent" with respect to a particular monoclonal antibody, as used herein, means a molecule that: (a) cross-blocks an exemplified monoclonal antibody; (b) binds selectively to the MenB PS derivative or glycoconjugate in question; (c) does not cross-react, or minimally cross-reacts, with host PSA as determined using the binding assays described herein; and, optionally, activity (e.g., complement-mediated bactericidal and/or opsonic activity) against MenB bacterial cells as determined by standard assays described below. Further, as used herein with regard to a particular monoclonal antibody-producing hybridoma of the invention, the term "progeny" is intended to include all derivatives, issue, and offspring of the parent hybridoma that produce the monoclonal antibody produced by the parent, regardless of generation or karyotypic identity.

Monoclonal antibodies are prepared using standard techniques, well known in the art, such as by the method of Kohler and Milstein, *Nature* (1975) 256:495, or a modification thereof, such as described by Buck et al. (1982) *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

More particularly, somatic cell hybrids can be prepared by the method of Buck et al., (supra), using the azaguanine resistant, non-secreting murine myeloma cell line P3X63-Ag8.653 (obtainable from the ATCC). The hybridoma cell lines are generally cloned by limiting dilution, and assayed for the production of antibodies which bind specifically to the immunizing antigen and which do not bind to unrelated antigens. The selected monoclonal antibody-secreting hybridomas are then cultured either in vitro (e.g., in tissue culture bottles or hollow fiber reactors), or in vivo (e.g., as ascites in mice).

Hybridoma supernatant can be assayed for anti-MenB PS derivative-reactive antibody using, for example, either solid phase ELISA or an indirect immunofluorescence assay with the immunizing MenB PS derivative or with native MenB PS (NAc-MenB PS). The selectivity of monoclonal antibodies secreted by the hybridomas can be assessed using competitive specific binding assays, such as inhibition ELISA, or the like. For example, antibody molecules, either diluted in buffer, or buffer containing soluble MenB PS derivatives or NAc-MenB PS, are reacted in an ELISA vessel in the presence of bound MenB PS derivatives. After washing, bound antibody is detected by labeled anti-Ig (anti-IgM, IgG and IgA) as the secondary antibody. Antibodies that are inhibited by the soluble MenB PS derivatives can be considered specific and, thus are selected for further study including, isotyping and additional screening for cross-reactivity, functional activity, and autoreactivity.

Specifically, partially purified monoclonal antibody molecules can be individually evaluated for their ability to bind to host cells which express polysialic acid residues on their cell surfaces. Such cells represent surrogate targets for the detection of antibodies that exhibit autoimmune activity. One target comprises the human neuroblastoma cell line, CHP-134, which expresses long chain $\alpha 2$–8 polysialic acid (NCAM) on its cell surface, as described by Livingston et al. (1988) *J. Biol. Chem.* 263:9443. Also, Granoff, D. M. et al. (1988) *The J. of Immunology* 160:5028–5036 describe bactericidal monoclonal antibodies that define unique MenB PS epitopes that do not cross-react with human polysialic acid. Other suitable targets include, but are not limited to, newborn brain cells, tissues derived from e.g., kidney, heart and the olfactory nerve, cultured saphenous vein endothelial cells, cytotoxic T lymphocytes and natural killer (NK) cells. See, e.g., Brandon et al. (1993) *Intl. J. Immunopathology and Pharmacology* 6:77. Monoclonal antibody molecules obtained from the hybridomas can be added to suitable test cell populations in culture, and the potential binding of the monoclonals to the cellular targets detected and quantified directly using labeled monoclonals, or indirectly using an appropriately labeled secondary reagent that reacts specifically with each monoclonal antibody (e.g., Staphylococcal Protein A and G and anti-murine antibody molecules). Antibodies that do not cross-react with test host tissue PSA or that display minimal reactivity are not considered autoreactive for purposes of the present invention. Thus, these antibodies are appropriate for further use. In addition, some antibodies that show binding with test tissue, which binding is not affected by pre-treatment of the test cells with neuraminidase, may also be appropriate for further use. Autoreactivity of such antibodies is termed "indeterminate" herein.

Functional activity can be determined by assessing complement-mediated bactericidal activity and/or opsonic activity. In particular, complement-mediated bactericidal activity of the antibodies can be evaluated using standard assays such as those described by Gold et al. (1970) *Infect. Immun.* 1:479, Westerink et al. (1988) *Infect. Immun.* 56:1120, Mandrell et al. (1995) *J. Infect. Dis.* 172:1279, and Granoff et al. (1995) *Clin. Diagn. Laboratory Immunol.* 2:574. In these assays, *N. meningitidis* is reacted with a complement source as well as with the antibody to be tested. Bacterial counts are done at various sampling times. Those antibodies that demonstrate complement-mediated bactericidal activity, as demonstrated by a minimum of a 50% reduction in viable bacterial cell counts determined after sixty minutes incubation with antibody and complement, as compared to colony counts at time zero, are considered to exhibit bactericidal activity for purposes of the present invention and are suitable for further use.

Complement-mediated bacteriolysis is thought to be the major mechanism responsible for host protection against invasive Meningococcal disease. However, evidence also supports an important protective role for opsonization (see, e.g., Bjerknes et al. (1 995) *Infect. Immun.* 63:160). Accordingly, the opsonic activity of the antibodies produced herein can be evaluated as a second measure, or as an alternative measure, to assess functional activity. Results from opsonic assays can be used to supplement bactericidal data, and to help in the selection of antibodies capable of conferring protection. Evaluation of opsonic activity is also particularly useful herein for the evaluation of the murine monoclonal antibodies of the invention which have an IgG1 isotype. Murine IgG1 (in contrast to human IgG1) is ineffective in activation of complement. Thus, murine IgG1 antibodies do not activate complement-mediated bacteriolysis of MenB in the above-described assays. However, functional activity of IgG1 anti-NPr-MenB PS monoclonal antibodies can be assessed by opsonization in the absence of complement.

A variety of opsonic assay methods are known in the art, and can be used to evaluate functional activity of the monoclonal antibodies of the present invention. Such standard assays include those described by Sjursen et al. (1987) *Acta Path. Microbiol. Immunol. Scand., Sec.* C 95:283, Halstensen et al. (1989) *Scand. J. Infect. Dis.* 21:267, Lehmann et al. (1991) *APMIS* 99:769, Halstensen et al. (1991) *NIPH Annals* 14:157, Fredlund et al. (1992) *APMIS* 100:449, Guttormsen et al. (1992) *Infect. Immun.* 60:2777, Guttormsen et al. (1993) *J. Infec. Dis.* 167:1314, Bjerknes et al. (1995) *Infect. Immun.* 63:160, Hayrinen et al. (1995) *J. Infect. Dis.* 171:1481, de Velasco et al. (1995) *J. Infect. Dis.* 172:262, and Verheul, A. F. M. (1991) "*Meningococcal LPS Derived Oligosaccharide-Protein Conjugate Vaccines, Immunochemical and Immunological Aspects,*" Thesis, Utrecht University, The Netherlands, pp. 112–135.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

Antibody molecule fragments, e.g., F(ab')$_2$, Fv, sFv and scFv molecules, that are capable of exhibiting immunological binding properties of the parent monoclonal antibody molecule can be produced using known techniques. Inbar et al. (1972) *Proc. Nat. Acad. Sci. USA* 69:2659; Hochman et al. (1976) *Biochem* 15:2706; Ehrlich et al. (1980) *Biochem* 19:4091; Huston et al. (1988) *Proc. Nat. Acad. Sci. USA* 85(16):5879; and U.S. Pat. Nos. 5,091,513 and 5,132,405, to Huston et al.; and 4,946,778, to Ladner et al.

In the alternative, a phage-display system can be used to expand the monoclonal antibody molecule populations in vitro. Saiki, et al. (1986) *Nature* 324:163; Scharf et al. (1986) *Science* 233:1076; U.S. Pat. Nos. 4,683,195 and 4,683,202; Yang et al. (1995) *J Mol Biol* 254:392; Barbas, III et al. (1995) *Methods: Comp. Meth Enzymol* 8:94; Barbas, III et al. (1991) *Proc Natl Acad Sci USA* 88:7978.

Once generated, the phage display library can be used to improve the immunological binding affinity of the Fab molecules using known techniques. See, e.g., Figini et al. (1994) *J. Mol. Biol.* 239:68.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. (1978) *Nature* 275:615, Goeddel et al. (1979) *Nature* 281:544, Goeddel et al. (1980) *Nucleic Acids Res.* 8:4057, European Application No. EP 36,776, U.S. Pat. No. 4,551,433, deBoer et al. (1983) *Proc. NatL. Acad. Sci. USA* 80:21–25, and Siebenlist et al. (1980) *Cell* 20:269.

Expression systems in yeast include those described in Hinnen et al. (1978) *Proc. Natl. Acad. Sci. USA* 75:1929, Ito et al. (1983) *J. Bacteriol.* 153:163, Kurtz et al. (1986) *Mol. Cell. Biol.* 6:142, Kunze et al. (1985) *J. Basic Microbiol.* 25:141, Gleeson et al. (1986) *J. Gen. Microbiol.* 132:3459, Roggenkamp et al. (1986) *Mol. Gen. Genet.* 202:302, Das et al. (1984) *J. Bacteriol.* 158:1165, De Louvencourt et al. (1983) *J. Bacteriol.* 154:737, Van den Berg et al. (1990) *Bio/Technology* 8:135, Kunze et al. (1985) *J. Basic Microbiol.* 25:141, Cregg et al. (1985) *Mol. Cell. Biol.* 5:3376, U.S. Pat. Nos. 4,837,148 and 4,929,555, Beach et al. (1981) *Nature* 300:706, Davidow et al. (1985) *Curr. Genet.* 10:380, Gaillardin et al. (1985) *Curr. Genet.* 10:49, Ballance et al. (1983) *Biochem. Biophys. Res. Commun.* 112:284–289, Tilbum et al. (1983) *Gene* 26:205–221, Yelton et al. (1984) *Proc. Natl. Acad. Sci. USA* 81:1470–1474, Kelly et al. (1985) *EMBO J.* 4:475479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. (1988) *J. Gen. Virol.* 69:765–776, Milleret al. (1988) *Ann. Rev. Microbiol.* 42:177, Carbonell et al. (1988) *Gene* 73:409, Maeda et al. (1985) *Nature* 315:592–594, Lebacq-Verheyden et al. (1988) *Mol. Cell. Biol.* 8:3129, Smith et al. (1985) *Proc. Natl. Acad. Sci. USA* 82:8404, Miyajima et al. (1987) *Gene* 58:273, and Martin et al. (1988) *DNA* 7:99. Numerous baculoviral strains and variants and corresponding permissive insect host cells from hosts are described in Luckow et al. (1988) *Bio/Technology* 6:47–55, Miller et al. (1986) GENERIC ENGINEERING, Setlow, J. K. et al. eds., Vol. 8, Plenum Publishing, pp. 277–279, and Maeda et al. (1985) *Nature* 315:592–594.

Mammalian expression can be accomplished as described in Dijkema et al. (1985) *EMBO J.* 4:761, Gorman et al. (1982) *Proc. Natl. Acad. Sci. USA* 79:6777, Boshart et al. (1985) *Cell* 41:521, and U.S. Pat. No. 4,399,216. Other features of mammalian expression can be facilitated as described in Ham et al. (1979) *Meth. Enz.* 58:44, Barnes et al. (1980) *Anal. Biochem.* 102:255, U.S. Pat. Nos. 4,767, 704, 4,657,866, 4,927,762, 4,560,655 and Reissued U.S. Pat. No. RE 30,985, and in International Publication Nos. WO 90/103430, WO 87/00195.

The anti-MenB antibodies of the present invention, described above, are conveniently used as receptors to screen diverse molecular libraries in order to identify molecular mimetics of unique epitopes from MenB. Methods for identifying mimetics in molecular libraries generally involve the use of one or more of the following procedures: (1) affinity purification with an immobilized target receptor; (2) binding of a soluble receptor to tethered ligands; and (3) testing soluble compounds directly in antigen competition assays or for biological activity. Molecules screened for molecular mimics include but are not limited to small organic compounds, combinatorial libraries of organic compounds, nucleic acids, nucleic acid derivatives, saccharides or oligosaccharides, peptoids, soluble peptides, peptides tethered on a solid phase, peptides displayed on bacterial phage surface proteins, bacterial surface proteins or antibodies, and/or peptides containing non-peptide organic moieties.

For example, libraries of diverse molecular species can be made using combinatorial organic synthesis. See, e.g., Gordon et al. (1994) *J. Med. Chem.* 37:1335. Examples include but are not limited to pyrrolidines; oligocarbamates (Cho et al. (1993) *Science* 261:1303); peptoids such as N-substituted glycine polymers (Simon et al. (1992) *Proc. Natl. Acad. Sci. USA* 89:9367); and vinylogous polypeptides (Hagihara et al. (1992) *J. Am. Chem. Soc.* 114:6568).

A variety of approaches, known in the art, can be used to track the building blocks as they are added during synthesis so that the history of individual library members can be determined. These approaches include addressable location on a photolithographic chip (oligocarbamates), a deconvolution strategy in which "hits" are identified through recursive additions of monomers to partially synthesized libraries (peptoids, pyrroli dines, peptides), and coding combinatorial libraries by the separate synthesis of nucleotides (Nielsen et al. (1 993) *J. Am. Chem. Soc.* 115: 9812) or other organic moieties (Ohlmeyer et al. (1993) *Proc. Natl. Acad. Sci. USA* 90:10922) ("tags"). The coded tags associated with each library member can then be decoded after a mimetic has been selected. For example, nucleic acid tags can be decoded by DNA sequencing.

Peptoid combinatorial libraries are particularly useful for identifying molecular mimetics of unique MenB epitopes. Peptoids are oligomers of N-substituted glycine (Simon et al. (1992) *Proc. Natl. Acad. Sci. USA* 89:9367) and can be used to generate chemically diverse libraries of novel molecules. The monomers may incorporate t-butyl-based side-chain and 9-fluorenyl-methoxy-carbonyl a-amine protection. The assembly of monomers into peptoid oligomers can be performed, for example, on a solid phase using the "submonomer method" of Zuckermann et al. (1992) *J. Am. Chem. Soc.* 114:10646. In this method, syntheses are conducted with Rink amide polystyrene resin (Rink et al. (1987) *Tetrahedron Lett.* 28:3787). Resin-bound amines are bromoacetylated by in situ activation of bromoacetic acid with diisopropyl-carbodiimide. Subsequently, the resin-bound bromoacetamides are displaced by addition of an amine. The amines may incorporate t-butyl-based protection of additional reactive groups. This two-step cycle is repeated until the desired number of monomers is added. The oligopeptide is then released from the resin by treatment with 95% trifluroacetic acid/5% water. The syntheses are performed, preferably, using a robotic synthesizer. See, e.g., Zuckermann et al. (1992) *Pept. Protein Res.* 40:498; and Zuckermann et al. (1996) *Methods in Enzymology* 267:437. In the alternative, oligomerization of the peptoid monomers may be performed by in situ activation by either benzotriazol-1-yloxytris (pyrrolidino)phosphonium hexafluorphosphate or bromotris(pyrrolidino) phosphonium hexafluorophosphate. In this alternative method, the other steps are identical to conventional peptide synthesis using α-(9-fluorenyl methoxycarbonyl) amino acids (see, e.g., Simon et al. (1992), supra).

Once the peptoid libraries are generated, they can be screened by, e.g., adding the monoclonal antibodies of the present invention, along with various pools of the combinatorial peptoids, to wells of microtiter plates coated with MenB PS derivatives or MenB bacteria, either alone or as glycoconjugates. After a period of incubation and a wash to remove unbound antibody, the presence of bound antibody is determined by standard ELISA assays. See, e.g., Harlow & Lane, *Antibodies: A Laboratory Manual* (1988), Cold Spring Harbor Laboratory, Cold Spring Harbor, N.Y., 553. Wells that do not contain bound antibody indicate the presence of peptoid mimetics that bind to the antibody. The particular identities of the peptoid mimetics in the pools are determined by recursively adding back monomer units to partially synthesized members of the libraries. Zuckermann et al. (1994) *J. Med. Chem.* 37:2678. Other methods for identifying active compounds in pools of small molecules include fractionating the pool by reverse phase HPLC or affinity selection/mass spectroscopy (Nedved M. L. Et al (1996) *Anal. Chem.* 68:4228).

Once putative molecular mimetics are identified, they are tested for their ability to elicit functionally active (e.g., bactericidal and/or opsonic) antibodies which lack autoreactivity or have minimal autoreactivity, as described above. Molecular mimetics that have these properties are appropriate for further use, for example, in vaccine compositions.

Molecular mimetics identified using the functionally active anti-MenB antibodies of the invention can be used to generate antibody reagents for use in diagnostic assays. For example, antibodies reactive with the molecular mimetics can be used to detect bacterial antigen in biological samples using immunodiagnostic techniques such as competition, direct reaction, or sandwich type assays. Such assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include revealing labels such as fluorescent, chemiluminescent, radioactive, enzymatic labels or dye molecules, or other methods for detecting the formation of a complex between the mimetic and the antibody or antibodies reacted therewith.

The aforementioned assays generally involve separation of unbound antibody in a liquid phase from a solid phase support to which mimetic-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more MenB molecular mimetics) under suitable binding conditions such that the component is sufficiently immobilized to the support. Sometimes, immobilization of the mimetic to the support can be enhanced by first coupling the mimetic to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the mimetics to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., MenB and/or *E. coli* K1 antibodies) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a mimetic according to the present invention. A biological sample containing or suspected of containing anti-MenB or *E. coli* K1 immunoglobulin molecules is then added to the coated wells. After a period of incubation sufficient to allow antibody binding to the immobilized mimetic, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound MenB/*E. Coli* K1 antigen ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the mimetics and antibodies specific for those mimetics form complexes under precipitating conditions. In one particular embodiment, the mimetics can be attached to a solid phase particle (e.g., an agarose bead or the like) using coupling techniques known in the art, such as by direct chemical or indirect coupling. The mimetic-coated particle is then contacted under suitable binding conditions with a biological sample suspected of containing antibodies for MenB and/or E. coli K1. Cross-linking between bound antibodies causes the formation of particle-mimetic-antibody complex aggregates which can be precipitated and separated from the sample using washing and/or centrifugation. The reaction mixture can be analyzed to determine the presence or absence of antibody-mimetic complexes using any of a number of standard methods, such as those immunodiagnostic methods described above.

In yet a further embodiment, an immunoaffinity matrix can be provided, wherein a polyclonal population of antibodies from a biological sample suspected of containing MenB and/or E. coli K1 antibodies is immobilized to a substrate. In this regard, an initial affinity purification of the sample can be carried out using immobilized antigens. The resultant sample preparation will thus only contain anti-MenB and/or E. Coli K1 moieties, avoiding potential non-specific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled molecules are contacted with the bound antibodies under suitable binding conditions. After any non-specifically bound mimetic has been washed from the immunoaffinity support, the presence of bound antigen can be determined by assaying for label using methods known in the art.

A particularly preferred method for diagnosing MenB and/or E. coli K1 infection using the present invention involves the use of strip immunoblot assay (SIA) techniques, such as those known in the art which combine traditional Western and dot blotting techniques, e.g., the RIBA® (Chiron Corp., Emeryville, Calif.) test. In these assays, one or more mimetics according to the present invention are immobilized as individual, discrete bands on a membranous support test strip. Visualization of anti-MenB and/or E. coli K1 reactivity in the biological sample is accomplished using anti-human IgG enzyme-conjugates in conjunction with a colorimetric enzyme substrate. Internal controls, such as anti-human IgM and human IgG, can also be present on the strip. The assay can be performed manually or used in an automated format.

The above-described assay reagents, including the mimetics of the invention or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

In addition, molecular mimetic compositions, unique (e.g., non-autoimmune) Men B epitopes identified using the molecular mimetics can be used herein to diagnose or prevent MenB disease in mammalian subjects. Particularly, vaccine compositions of the molecular mimetics can be used for the prevention of MenB disease in vaccinated subjects.

The vaccine compositions can comprise one or more of the molecular mimetics or non-autoimmune epitopes of MenB. The vaccines may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Adjuvants may also be used to enhance the effectiveness of the vaccines. Adjuvants can be added directly to the vaccine compositions or can be administered separately, either concurrently with or shortly after, vaccine administration. Such adjuvants include, but are not limited to: (1) aluminum salts (alum), such as aluminum hydroxide, aluminum phosphate, aluminum sulfate, etc.; (2) oil-in-water emulsion fonnulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL +CWS (Detox™); (3) saponin adjuvants, such as Stimulon™ (Cambridge Bioscience, Worcester, Mass.) may be used or particle generated therefrom such as ISCOMs (immunostimulating complexes); (4) Freund's Complete Adjuvant (FCA) and Freund's Incomplete Adjuvant (FICA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanyl-D-isogluatme (nor-MDP), N-acetylmuramyl-L-alanyl-D-isogluatminyl-L-alanine-2-(1'- 2'-dipalmitoyl-sn-glycero-3-huydroxyphosphoryloxy)-ethylamine (MTP-PE), etc.

In order to enhance the effectiveness of compositions formed from a molecular mimetic, it may be necessary to conjugate the mimetic to a carrier molecule. Such carrier molecules will not themselves induce the production of harmful antibodies. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), inactive virus particles, $CRM_{197}$ (a nontoxic mutant diphtheria toxin), and the like. Such carriers are well known to those of ordinary skill in the art. The mimetic conjugates are selected for their ability to express epitopes that closely resemble those found on the surface of MenB bacterial cells. Suitable conjugates thus elicit the formation of antibodies that have functional activity against bacteria, and do not cross-react, or are minimally cross-reactive with polysialic acid in host tissue as determined using the binding assays described herein.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes, or adsorbed to particles for enhanced adjuvant effect, as discussed above.

The vaccines will comprise an effective amount of the molecular mimetic, and any other of the above-mentioned components, as needed. By "an effective amount" is meant an amount of a molecule which will induce an immunological response in the individual to which it is administered and poses a minimal risk of stimulating an autoimmune response in the individual. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or gd T cell populations.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of "Sized" Glycoconjugates

An exemplary NPr-MenB oligosaccharide-tetanus toxoid conjugate vaccine, hereinafter referred to as CONJ-2, was prepared as follows. The N-acetyl groups of MenB B polysaccharide were removed by heating the polysaccharide to 110° C. in 2M NaOH for 6 hours in the presence of $NaBH_4$. The de-acetylated polysaccharide was exhaustively dialyzed in saturated sodium bicarbonate buffer then stirred with an excess of propionic anhydride for 12 hours at ambient temperature. The solution was exhaustively dialyzed in water and the N-propionylated meningococcal B (NPr-MenB PS) polysaccharide was recovered by lyophilization.

For preparation of the conjugate vaccine, the NPr-MenB polysaccharide was partially hydrolyzed in 10 mM sodium acetate at pH 5.5 at 50° C. for 2 hours. The resulting mixture of oligosaccharides was fractionated on Q-Sepharose. Oligosaccharides having an average degree of polymerization (Dp) of 2–6 were first eluted with 100 mM NaCl and discarded. Intermediate-sized oligosaccharides were eluted with 500 mM NaCl. It was subsequently determined by analytical ion exchange chromatography using a MonoQ column that the intermediate-sized oligosaccharides ranged in size from Dp 13 to 20 (Mean=Dp 13).

A terminal aldehyde group was generated at the non-reducing end of the intermediate-sized oligosaccharides by reacting them with 100 mM sodium periodate for 15–30 minutes at ambient temperature in the dark. Excess ethylene glycol was used to quench the oxidative reaction and the product was desalted on a Sephadex G-25 column. The oligosaccharide-protein conjugate was prepared by stirring a mixture of terminal aldehyde containing NPr MenB oligosaccharide with tetanus toxoid (molar ratio of 200:1, respectively) in 0.75 M potassium phosphate buffer, pH 9.0 with 40 mg/ml of sodium cyanoborohydride for one day at 40° C. and two days at ambient temperature. The resultant NPr-MenB oligosaccharide-tetanus toxoid conjugate (CONJ-2) was finally purified by gel permeation chromatography on Sephadex G-100 using 50 mM sodium phosphate, pH 7.0, 150 mM sodium chloride as the eluting buffer. Sialic acid and protein compositions of the conjugate vaccine were measured by the Svennerholm resorcinol reaction (Svennerholm, L. (1957) *Biochim. Biophys. Acta.* 24:604) and Lowry assays, respectively. On a weight basis, the final saccharide-to-protein ratio of the CONJ-2 conjugates ranged from 0.10 to 0.25.

EXAMPLE 2

Characterization of the Glycoconjugates

The CONJ-2 glycoconjugate was characterized as follows. In order to demonstrate covalence (e.g., establishing a covalent linkage between the NPr-MenB OS and the protein carrier), a number of physico-chemical techniques can be used, including: SDS-PAGE; Western Blot; Sephadex G-100 gel filtration; or the like. For the purposes of the present study, SDS-PAGE was used to establish covalent attachment of the NPR-MenB OS/TT CONJ-2 glycoconjugates by revealing a shift to higher molecular weight for the conjugate band as compared to the carrier protein band, per se. Western blot analysis of the CONJ-2 glycoconjugates demonstrated covalence by the coincidence of positive immunoreactive signals for TT and NPr-MenB PS with specific anti-TT and anti-NPr-MenB PS antisera.

Based on steric factors, the use of oligosaccharides instead of large molecular weight polysaccharides in the preparation of the CONJ-2 glycoconjugates allows for higher coupling efficiency of saccharide antigens onto the protein carrier molecule. The final saccharide-to-protein ratio of these NPr-MenB oligosaccharide-based conjugates range from about 0.10 to 0.25 which corresponds to about 3 to 5 NPr-MenB oligosaccharide chains covalently bound per protein carrier. On a per weight basis, the CONJ-2 glycoconjugates appear to have a higher saccharide loading than a previously reported NPr-MenB polysaccharide-based conjugate (U.S. Pat. No. 4,727,136) wherein CONJ-2 contains, on the average, about 7.5 to 18.8 times more saccharide (using 10,000 Daltons as the molecular weight of NPr-MenB PS).

In addition, constructing the CONJ-2 glycoconjugates to have substantially homogenous-sized saccharide moieties of a well-defined intermediate chain length (e.g., average Dp of 10–20) is expected to result in glycoconjugates which display more consistent immunological behavior. Further, the selective end-activation (e.g., selective introduction of the aldehyde group at the non-reducing terminus) of the Q-Sepharose chromatography-purified NPr-MenB oligosaccharides avoids the possibility of cross-linked, heterogenous structures which could arise from the use of NPr-MenB PS molecules with "active" aldehyde groups introduced at both termini. In this regard, it is likely that bi-terminally activated PS (having aldehyde groups at both ends) could be derived from a periodate oxidation of N-acylated MenB PS previously exposed to $NaBH_4$ during the N-deacetylation procedure.

EXAMPLE 3

Preparation of Monoclonal Antibodies 4 to 6 week old female CD1 mice were vaccinated by ip injection using a composition containing an NPr-MenB OS/TT (CONJ-2) glycoconjugate antigen and (except for the last booster injection) FCA. Vaccinations were administered at one month intervals for a total of 2 or 3 dosages (including the booster immunization). Three days prior to fusion, the primed animals were boosted with the NPr-MenB OS/TT (CONJ-2) glycoconjugate antigen in the absence of adjuvant. The final volume of each dose was 0.1 ml, which contained 2.5 $\mu$g of sialic acid. After the booster injection, the animals were splenectomized and the spleen cells were prepared for fusion with myeloma cells.

Approximately one week before fusion, non-secreting murine P3X63-Ag8.653 myeloma cells (available from the ATCC under accession number ATCC-1580-CRL), were expanded in complete RPMI-1640 medium with 25 mM HEPES buffer and L-Glutamine (GIBCO BRL 041-02400). The cell cultures were assessed periodically to monitor cell growth, cell numbers and to screen for contamination.

On the day of fusion, the spleen cells and the partner P3X63-Ag8.653 myeloma cells (Ag8 cells) were washed, harvested and mixed at a ratio of 5:1 (spleen cells:myeloma cells). The cell fusions were performed at 37° C. in the presence of 50% polyethylene glycol (PEG). The resulting cell pellets were harvested and plated into 96 well flat-bottom cell culture plates (COSTAR 3596) and incubated under suitable conditions (e.g., at 37° C. in 5% $CO_2$). After one day of incubation, selective medium containing hypoxanthine, aminopterin and thymidine (HAT) was added to each well.

Hybridomas from wells containing growing cells and exhibiting about 10 to 25% confluence were selected for screening after about two weeks of incubation in the HAT selective medium. Selected hybridoma supernatants were screened using a solid phase avidin-biotinylated NPr-MenB PS based ELISA assay. Specificity of antibody binding in the supernatants was determined using soluble NPr-MenB PS as the inhibitor. Negative controls included RPMI medium, Ag8 myeloma supernatant and irrelevant monoclonal antibody preparations. Pooled polyclonal sera from mice immunized with the NPr-MenB OS/TT (CONJ-2) glycoconjugate was used as the positive control. After overnight incubation with the supernatants, the reaction wells were washed and bound immunoglobulin was detected with alkaline phosphatase-labelled polyvalent anti-murine immunoglobulins (IgG, IgA, IgM).

Candidate hybridomas were identified based on their demonstrated binding affinity for NPr-MenB PS in the above-described ELISA assay. Hybridomas secreting highly reactive antibody molecules were cloned by limiting dilution. Particularly, candidate hybridoma cell lines were plated at 0.3, 1.0 and 3.0 cell/well in Terasaki plates (NUNC) in 20 $\mu$l of cloning/expansion medium (Complete RPMI-1640 with IL6). After two weeks, the cultures were visually inspected for growth. Frequency analysis was performed using the least squares method described by Lefkovits et al. (1984) Immun. Today 5(9):265. The ELISA assay used to identify reactive supernatant among the master wells was repeated to assess antibody activity on days 7 and 14. Selected clones were then expanded and frozen for subsequent use in tissue culture and ascites production. A panel of 39 hybridomas was thus produced, and the secreted monoclonal antibody molecules obtained therefrom (termed "SEAM monoclonal antibodies," particularly, monoclonal antibodies SEAM-1 through SEAM-24, SEAM-26, SEAM-28 through SEAM-31, SEAM-33 through SEAM-36, SEAM-38 through SEAM-42, and SEAM-48) were prepared for further evaluation.

More particularly, selected monoclonal antibodies were produced either in tissue culture, or in ascitic fluid using Pristane-primed 7 to 8 week old male Balb/c mice. Each animal subject was primed by i.p. injection with 0.5 ml Pristane one week prior to inoculation with hybridoma cells. Prior to inoculation, the hybridoma cell concentrations were adjusted to between $2.5 \times 10^6$ and $3 \times 10^6$ cells/ml using sterile PBS. The primed animals were injected i.p. with 1 ml of hybridoma cells, wherein each clonal cell line was inoculated into three different mice. One to two weeks after inoculation, ascites fluid collection was started and continued for a period of approximately one week. The collected fluid was centrifuged at ambient temperature for 10 minutes at 2700 rpm (1500×g). Supernatants were harvested and pellets discarded. The isolated ascites fluid was stored at 4° C. over the course of collection, and fluid collected on different days was pooled, aliquoted and frozen at –70° C.

EXAMPLE 4

Characterization of the Monoclonal Antibodies

The concentrations of unpurified monoclonal antibodies were determined using an ELISA capture assay and a radial immunodiffusion assay. Particularly, a capture ELISA procedure was used to determine the concentration of each of the anti-NPr-McnB PS monoclonal antibodies. Microtiter plates (Immulon 2, available from Dynatech Laboratories, Inc.) containing 100 $\mu$l/well of affinity purified rabbit anti-murine IgG, IgM and IgA (H and L, Zymed) diluted to 1 $\mu$g/ml in 10 mM PBS (pH 7.4) were incubated overnight at 4° C. After washing three times with PBS, the wells were filled with 250 $\mu$l of Blocking Buffer (PBS containing 1% bovine serum albumin (BSA) and 0.1 % sodium azide, pH 7.4) and incubated for 30 to 60 minutes at ambient temperature to block nonspecific binding sites. The plates were washed three times with Washing Buffer (PBS containing 0.1 % Tween 20 and 0.1% sodium azide, pH 7.4). Antibodies to be tested were diluted in Diluting Buffer (PBS containing 1% BSA, 0.1% Tween 20 and 0.1% sodium azide, pH 7.4) and then added at 100 $\mu$l per each well. The plates were covered and incubated overnight at 4° C. Murine IgG1, IgG2b, IgG3 and IgM immunoglobulin standards (available from Southern Biotechnology Associates), at concentrations ranging from 500 ng/ml to 4 ng/ml, were used to construct standard curves for quantifying antibody concentrations.

After incubation overnight, the wells were washed five times with cold Washing Buffer and incubated for 3 hours at 4° C. with 100 μl/well of alkaline phosphatase conjugated anti-murine IgG, IgM and IgA polyclonal antibodies (H and L, Zymed) that were diluted 1:2000 in Diluting Buffer. The plates were then washed with cold Washing Buffer, and 100 μl of freshly prepared substrate (p-Nitrophenyl phosphate, Sigma) diluted to 1 mg/ml in Substrate Buffer (1.0 M diethanolamine, 0.5 mM $MgCl_2$, pH 9.8) was added to each well. Absorbance values at 405 nm were measured after approximately 30 minutes. Immunoglobulin concentrations of the monoclonal antibody preparations were calculated from the standard curves.

Radial immunodiffusion assays were conducted as follows. Radial immunodiffusion plates and reagents were obtained from The Binding Site Limited (Birmingham, England). The assay protocol was then based on the manufacturer's specific instructions supplied with the RID kit. Briefly, calibrator antibody supplied with the kit was reconstituted with an appropriate amount of distilled water. 1:2 and 1:10 dilutions of calibrator antibody were prepared. Test samples can be diluted in 1% BSA if necessary. Aliquots of 10 μl (20 μl for IgA and IgG2a subclass antibodies) for calibrator antibody (neat, 1:2, and 1:10 dilutions) and test samples were applied to separate wells on the plate and incubated for 120 hours at room temperature. The concentrations of the antibodies were determined by measuring the precipitation ring diameters and comparing these values to a reference table included with the RID kit.

The monoclonal antibodies from tissue culture or ascitic fluid were then partially purified as follows. Tissue culture supernatant or ascites containing the monoclonals (200 ml or indicated volume) was added slowly to an equal volume of cold 100% saturated ammonium sulfate (SIGMA, Saint Louis, Mo.) while stirring the solution gently. The monoclonal antibody and Ammonium sulfate mixture was incubated overnight at 4° C. The following morning, the mixture was stirred gently to homogeneity and centrifuged at 5000 rpm in a Sorvall SS34 rotor for 30 minutes at 4° C. After decanting the supernatant, an equal volume of 50% ammonium sulfate solution (i.e. same volume as the 100% saturated ammonium sulfate) was used to wash and resuspend the pellet. The resulting mixture was centrifuged at 5000 rpm in a Sorvall SS34 rotor for 30 minutes at 4° C. The supernatant was then decanted and drained.

For ascites, the pellet was reconstituted in 0.3–0.5 volumes of the starting volume in PBS Buffer (50 mM sodium phosphate, 150 mM sodium chloride, pH 7.4). For tissue culture supernatant, the pellet was reconstituted in 0.1 volumes of the starting volume of PBS Buffer. The reconstituted monoclonal antibody and ammonium sulfate mixture was placed in a dialysis tubing (molecular weight cut off 10,000–12,000) and allowed to dialyze in 4 L of PBS overnight. The PBS solution was changed 3 to 4 times over the following two days. Monoclonal antibody molecules from the dialysis tubes were transferred into a syringe and sterile filtered through a 0.2 μm membrane filter, and then stored at −20° C.

The partially purified monoclonal antibody preparations were then characterized for: (a) immunoglobulin isotype, (b) concentration-dependent binding to NPr-MenB PS, (c) the ability of various NPr-MenB oligomers to inhibit binding to NPr-MenB PS, (d) cross-reactivity with native MenB PS, (e) cross-reactivity with virulent strains of MenB, (f) complement-mediated bactericidal activity, (g) opsonic activity, and (h) autoreactivity as demonstrated by binding to a neuroblastoma cell line that expresses long chain α2–8 linked polysialic acid at the cell surface. In these experiments, the concentrations of monoclonal antibody were measured by the capture ELISA and RID assay described above.

(a) Isotyping of the Antibodies:

The isotypes of the monoclonal antibodies (heavy and light chains) were determined by ELISA using the above-described protocol for the anti-NPr-MenB PS ELISA with the only difference that the secondary alkaline phosphatase-conjugated antibody was specific for IgG subclasses, IgM, IgA and κ and λ light chains. A kit was also used to isotype the antibody molecules. The kit consisted of typing stick substrates coated with goat antibodies specific for the different types of immunoglobulin peptide chains. The kit provides a peroxidase-labelled species specific for anti-murine immunoglobulin to detect the murine monoclonal antibodies bound to the goat antibodies on the substrate.

As depicted below in Table 1, the isotypic distribution among the 39 monoclonal antibodies was found to consist of one IgM and thirty-eight IgG (eight IgG1, five IgG2a, sixteen IgG2b, and nine IgG3). In addition, all antibody molecules had κ light chains.

TABLE 1

| Fine Antigenic Specificity Group (a) | SEAM Monoclonal Antibody Number | Ig Isotype | ELISA Reactivity to N-Pr-MenB PS (b) | ELISA Inhibition of N-Pr-MenB Binding by N-Pr-MenB OS (c) | ELISA Reactivity to N-Ac-MenB PS (d) | Binding to Encapsulated Neisseria meningitidis group B (e) | Binding to CHP134 PSA (f) | Bactericidal Activity (g) | Opsono-phagocytotic Activity (g) |
|---|---|---|---|---|---|---|---|---|---|
| I | 10 | G1, κ | +++ | +++ | ++ | + | 0 | ND | 0 |
| | 11 | G2b, κ | +++ | ++ | +++ | + | ++ | ++ | ND |
| | 18 | G2b, κ | +++ | +++ | +++ | + | + | +++ | ++ |
| | 20 | G2b, κ | +/− | ++ | ++ | 0 | 0 | 0 | ND |
| | 21 | G2b, κ | ++++ | +++ | ++ | 0 | 0 | 0 | ND |
| | 26 | G2b, κ | ++++ | + | +++ | + | ++ | ++ | ND |
| | 28 | G2b, κ | ++++ | ++ | ++ | + | + | ++ | ++ |
| | 29 | G2a, κ | ++++ | ++ | ++ | + | ++ | 0 | ND |
| | 35 | G2b, κ | ++++ | + | +++ | + | ++ | +++ | ++ |
| II | 12 | G2a, κ | ++++ | 0 | ++ | + | + | +++ | ++ |
| | 13 | G3, κ | +++ | 0 | +++ | + | ++ | +++ | ++++ |
| | 14 | G2b, κ | ++++ | 0 | +++ | + | ++ | ++ | ND |
| | 15 | G2b, κ | ++++ | 0 | +++ | + | ++ | ++ | ND |
| | 16 | G2b, κ | +++ | 0 | + | + | i | ++ | 0 |
| | 30 | G3, κ | +++ | 0 | +++ | + | ++ | +++ | ++++ |
| III | 1 | G3, κ | + | + | 0 | 0 | 0 | ++ | ND |
| | 3 | G2b, κ | ++++ | +++ | 0 | + | 0 | ++ | ++++ |
| | 4 | G1, κ | ++ | ++ | 0 | i | i | ND | ND |

TABLE 1-continued

| Fine Antigenic Specificity Group (a) | SEAM Monoclonal Antibody Number | Ig Isotype | ELISA Reactivity to N-Pr-MenB PS (b) | ELISA Inhibition of N-Pr-MenB Binding by N-Pr-MenB OS (c) | ELISA Reactivity to N-Ac-MenB PS (d) | Binding to Encapsulated *Neisseria meningitidis* group B (e) | Binding to CHP134 PSA (f) | Bactericidal Activity (g) | Opsono-phagocytotic Activity (g) |
|---|---|---|---|---|---|---|---|---|---|
| | 5 | G3, κ | +/− | + | 0 | + | 0 | +++ | 0 |
| | 7 | G3, κ | + | + | 0 | i | i | +++ | 0 |
| | 8 | G3, κ | +++ | +++ | 0 | + | 0 | +++ | 0 |
| | 17 | M, κ | + | +++ | 0 | 0 | 0 | 0 | ND |
| | 19 | G2a, κ | ++ | ++ | 0 | 0 | i | 0 | ND |
| | 22 | G2b, κ | + | ++ | 0 | 0 | i | 0 | ND |
| | 23 | G2b, κ | ++ | + | 0 | 0 | 0 | 0 | ND |
| | 48 | G2b, κ | +++ | +++ | 0 | + | 0 | ++ | ++ |
| IV | 2 | G3, κ | +/− | 0 | 0 | + | 0 | +++ | 0 |
| | 6 | G3, κ | +/− | 0 | 0 | 0 | i | 0 | ND |
| | 9 | G1, κ | ++ | 0 | 0 | 0 | i | ND | ND |
| | 24 | G2b, κ | ++ | 0 | 0 | + | 0 | 0 | ND |
| ND | 31 | G1, κ | +/− | ND | + | + | i | ND | ND |
| | 36 | G2a, κ | +++ | ND | ++ | + | ++ | ++ | ND |
| | 39 | G2a, κ | +/− | ND | ++ | 0 | ++ | 0 | ND |
| | 40 | G1, κ | ++++ | ND | + | + | ++ | 0 | ND |
| | 41 | G2b, κ | ++ | ND | + | + | 0 | ++ | 0 |
| | 33 | G1, κ | + | ND | 0 | 0 | 0 | ND | ND |
| | 34 | G3, κ | +/− | ND | 0 | 0 | 0 | 0 | ND |
| | 38 | G1, κ | +/− | ND | 0 | 0 | 0 | ND | ND |
| | 42 | G1, κ | +/− | ND | 0 | + | i | ND | ND |

*The data reported in Table 1 represent the results of repeated studies as described herein, and are subject to some variance due to use of different antigen sources in the ELISA procedure, and different complement sources in the bactericidal assay.
(a) Defined by cross-reactivity with N-Ac-MenB PS by ELISA and inhibition of anti-N-Pr-MenB PS binding by short N-Pr-MenB oligomers.
(b) Concentration of monoclonal antibody required to yield an OD of 0.5: +/−, 5–25 μg/ml; +, 1.0–4.9 μg/ml; ++, 0.1–0.9 μg/ml; +++, 0.01–0.09 μg/ml; ++++, <0.01 μg/ml.
(c) 0, <25% inhibition; +, 26–48% inhibition; ++, 49–74% inhibition; +++, 75–100% inhibition when tested at OD 0.5 to 1; Dp 3.8 N-Pr-MenB fragments.
(d) 0, OD < 0.15; +, OD 0.15–0.5; ++, OD 0.5–1.0; +++, OD > 1.0 when tested at 5 to 25 μg/ml of antibody by ELISA.
(e) 0, no detectable binding to encapsulated strains when tested at 100 μg/ml; +, binding to encapsulated strains 8047 and NmB, but not to non-encapsulated strain M7; i, indeterminate (see text).
(f) 0, no binding activity to polysialic acid (PSA) when tested at 100 μg/ml of antibody; ++, binding activity when tested at 10 μg/ml and inhibitable by neuraminadase treatment; +, binding activity detected at 100 but not 10 μg/ml; i, indeterminate is binding activity not inhibitable by neuraminadase treatment.
(g) ++++, activity with both rabbit and human complement, and in the absence of complement; +++, activity with both rabbit and human complement; ++, activity with rabbit complement, no activity with human complement; 0, no activity with rabbit complement or human complement (also includes antibodies only tested with rabbit complement); ND, not done.

(b) Concentration-Dependent Binding to NPr-MenB PS.

A solid phase ELISA procedure was used to assess the concentration dependent binding of the antibody molecules to NPr-MenB PS in the presence of buffer alone or 25 μg/ml of a soluble NPr-MenB PS inhibitor. Biotinylated NPr-MenB PS-ADH was prepared using the method of Sutton et al. (1985) *J. Immunol. Methods* 82:215. Microtiter plates (Immulon 2, available from Dynatech Laboratories, Inc.) containing 100 μl/well of avidin (4 μg/ml Extr Avidin, Sigma) in 10 mM PBS (pH 7.4) were incubated overnight at 4° C. After washing three times with PBS, 100 μl of biotinylated NPr-MenB PS in PBS was added to each well and incubated at 37° C. for 2 hours. The plates were washed three times with PBS, and the wells were filled with 250 μl of Blocking Buffer and incubated for 30 to 60 minutes at ambient temperature to block nonspecific binding sites.

After blocking, the plates were washed three times with Washing Buffer. 50 μl aliquots of various dilutions of the monoclonals were added to wells of replicate plates containing either 50 μl of Diluting Buffer or 50 μl of Diluting Buffer containing 50 μg of soluble NPr-MenB PS per ml (for a final inhibitor concentration of 25 μg/ml). The plates were then covered and incubated overnight at 4° C. On the following day, the wells were washed five times with cold Washing Buffer and then incubated for 3 hours at 4° C. with 100 μl/well of alkaline phosphatase conjugated anti-murine IgG, IgM and IgA polyclonal antibodies (Zymed) diluted 1:2000 in Diluting Buffer. The plates were then washed with cold Washing Buffer, and 100 μl of freshly prepared substrate (p-Nitrophenyl phosphate, Sigma) diluted to 1 mg/ml in Substrate Buffer was added to each well. Absorbance values at 405 nm were measured after approximately 30 minutes.

Table 1 summarizes the respective concentration ranges of antibody required to yield an OD of 0.5 in an ELISA for each of the 39 SEAM monoclonal antibodies. The most likely explanation for the large heterogeneity in the values shown is differences in antibody avidity to NPr-MenB PS.

(c) Inhibition of Antibody Binding to NPr-MenB PS by Oligomers:

A competitive solid phase ELISA procedure was used to assess the ability of NPr-MenB oligomer inhibitors to inhibit binding of the monoclonal antibody molecules to solid phase NPr-MenB PS. The assay was performed as described above for the anti-NPr-MenB PS ELISA with the exception that the monoclonal antibodies were pre-diluted to concentrations to yield an OD of 0.5 to 1. The monoclonal antibodies were added to wells of replica plates, each containing one of the following soluble inhibitors to yield a final inhibitor concentration of 25 μg/ml: high molecular weight (HMW) NPr-MenB PS; or low molecular weight (LMW) NPr-MenB OS (having an average Dp of 3.8).

The plates were covered and incubated overnight at 4° C. On the following day, the wells were washed five times with cold Washing Buffer and then incubated for 3 hours at 4° C. with 100 μl/well of alkaline phosphatase conjugated anti-murine IgG, IgM and IgA polyclonal antibodies (Zymed) diluted 1:2000 in Diluting Buffer. The plates were then washed with cold Washing Buffer, and 100 µl of freshly prepared substrate (p-Nitrophenyl phosphate, Sigma) diluted to 1 mg/ml in Substrate Buffer was added to each well. Absorbance values at 405 nm were measured after approximately 30 minutes. Percent inhibition was calculated as compared to binding in the absence of inhibitor.

The HMW NPr-MenB PS inhibitor provided approximately 75% to 95% inhibition in all monoclonal antibodies tested. Differences in fine antigenic specificity in the monoclonal antibodies are evident from the different respective patterns of inhibition with the LMW inhibitor tested. For example, binding of SEAM-3 and SEAM-18 to NPr-MenB PS is completely inhibited by the soluble LMW inhibitor of NPr-MenB PS. In contrast, SEAM-2 and SEAM-16 are not significantly inhibited by the oligomers (less than 20%). The results of LMW NPr-MenB OS inhibition for all of the monoclonal antibodies are depicted in Table 1. In addition, as described below, other differences in the fine antigenic specificity of the monoclonals are evident by the differences observed in cross-reactivity to NAc-MenB PS in ELISA and differences in binding to host polysialic acid.

(d) Cross-Reactivity with NAc-MenB PS:

The monoclonal antibodies were evaluated for their ability to cross-react with the NAc-MenB polysaccharide as demonstrated by direct binding to NAc-MenB PS in a solid phase ELISA format. The method used was similar to that described above for the NPr-MenB PS ELISA, with the exception that NAc-MenB PS-ADH was used as the solid phase antigen instead of biotinylated NPr-MenB PS.

50 µl aliquots of various dilutions of the monoclonals were added to wells of replicate plates containing either 50 µl of Diluting Buffer or 50 µl of Diluting Buffer containing 50 µg of soluble NAc-MenB PS per ml (for a final inhibitor concentration of 25 µg/ml). The plates were then covered and incubated overnight at 4° C. On the following day, the wells were washed five times with cold Washing Buffer and then incubated for 3 hours at 4° C. with 100 µl/well of alkaline phosphatase conjugated anti-murine IgG, IgM and IgA polyclonal antibodies (Zymed) diluted 1:2000 in Diluting Buffer. The plates were then washed with cold Washing Buffer, and 100 µl of freshly prepared substrate (p-Nitrophenyl phosphate, Sigma) diluted to 1 mg/ml in Substrate Buffer was added to each well. Absorbance values at 405 nm were measured after approximately 30 minutes.

The cross-reactivity of each of the 46 monoclonal antibodies with the NAc-MenB PS was scored over a range of (++) for highly cross reactive, to (0) for non cross-reactive. The results are depicted in Table 1. As can be seen, sixteen of the monoclonal antibodies cross-reacted with the NAc-MenB PS, and four minimally cross reacted (±). Specificity of the cross-reactivity of these twenty positive, or weakly positive monoclonal preparations was confirmed by inhibition of binding using soluble NAc-MenB PS. The 26 non cross-reactive monoclonal antibodies showed no significant binding to solid phase NAc-MenB PS when tested at antibody concentrations up to 25 µg/ml.

(e) Bacterial Binding Assay:

The ability of the anti-N-Pr meningococcal B polysaccharide antibodies to bind to the surface of pathogenic strains of N. meningitidis Group B was determined using flow cytometric detection of indirect immunofluorescence assay. Two fully encapsulated meningococcal B test organisms were used, strain 8047 (the strain used to measure bactericidal activity, see below) and NmB. A third unencapsulated strain, M7, which is a transposon-containing mutant of NmB (Stephens et al. (1991) Infect. & Immun. 59:4097–4102) was used as a negative control for specificity of antibody binding to the capsular polysaccharide. Bacterial cells grown to mid-log phase in Mueller-Hinton broth and 0.25% glucose were harvested and resuspended in Blocking Buffer at a density of ~$10^8$ cells per ml. The monoclonal antibodies (concentration of 10 or 100 µg/ml) were then added and allowed to bind to the cells on ice for 2 hours. Following two washes with Blocking Buffer, the cells were incubated with FITC-conjugated F(ab')$_2$ fragment goat anti-mouse IgG (H+L) (Jackson Immune Research, West Grove, Pa.), fixed with 0.25% formaldehyde in PBS buffer, and analyzed by flow cytometry.

Positive control antibodies included meningococcal- specific serotyping and subtyping monoclonal antibodies (MN2C3B, MN16C13F4, RIVM, Bilthoven, the Netherlands). The negative control consisted of a mouse IgG monoclonal antibody of irrelevant specificity.

As summarized in Table 1, twenty-four of the anti-N-Pr meningococcal B polysaccharide antibodies showed evidence of bacterial binding when tested at 100 µg/ml. Two additional antibodies showed evidence of minimal binding to both encapsulated and non-encapsulated mutant strains. Bacterial binding of these antibodies was scored as indeterminant (i).

(f) Complement-Mediated Bactericidal Activity:

A bactericidal assay was conducted using the methods described by Mandrell et al. (1995) J. Infec. Dis. 172:1279, with the following modifications: the organism was grown in Mueller-Hinton broth containing 0.25% glucose; and serum diluting buffer consisted of Gey's buffer instead of barbitol buffer. In several experiments, different sources of complement were used: these included two different infant rabbit serum pools (referred to as Rab C I and Rab C II) and human agammaglobulinemic serum (referred to as Hu C).

The ability of each of the monoclonal antibodies to activate complement-mediated bacterial lysis is reported in Table 1. There are examples of bactericidal antibodies that cross react with NAc-MenB PS by ELISA (e.g., SEAM-18, SEAM-30, and SEAM-35). There also are examples of bactericidal antibodies that show no cross-reactivity with NAc-MenB PS (e.g., SEAM-2, SEAM-5, SEAM-7, and SEAM-8).

(g) Opsonic Activity:

Opsonic activity of the monoclonal antibodies can be measured by a variety of established methods. Sjursen et al. (1987) Acta Path. Microbiol. Immunol. Scand., Sec. C 95:283, Halstensen et al. (1989) Scand. J. Infect. Dis. 21:267, Lehmann et al. (1991) APMIS 99:769, Halstensen et al. (1991) NIPH Annals 14:157, Fredlund et al. (1992) APMIS 100:449, Guttormsen et al. (1992) Infect. Immun. 60:2777, Guttormsen et al. (1993) J. Infec. Dis. 167:1314, Bjerknes et al. (1995) Infect. Immun. 63:160, and Hayrinen et al. (1995) J. Infect. Dis. 171:1481.

In one opsonization assay, N. meningitidis freshly grown on GN agar plates (Greiner Labortechniek, Greiner BV, Alphen a/d Rijn, Netherlands) at 37° C. was used to inoculate 8 ml of Mueller Hinton broth (Difco, Detroit, Mich.) to obtain an initial OD of 0.1. The bacteria were grown to log phase (660 nm absorbance of 0.75–0.85) with vigorous shaking. The cells were transferred to sterile plastic tubes with caps and centrifuged for 10 minutes at 3500 rpm.

Cells were fixed by adding 4 ml of 70% ethanol and incubating for at least 1 hour 4° C. The fixed cells were again pelleted by centrifugation for 10 minutes at 3500 rpm and resuspended in sterile phosphate buffered saline (PBS) to yield an OD of 1.0. The cell suspension (1.35 ml) was added to an eppendorf tube and centrifuged for 5 minutes at 10,000 rpm. The supernatant was discarded, and another 1.35 ml was added to the same tube followed by centrifugation to yield $1 \times 10^9$ cells per tube. A 1.0 mg/ml solution of fluorescein isothiocyanate (FITC) in PBS (Sigma, St. Louis, M0.) was prepared and sonicated for 5 minutes, then centrifuged for 5 minutes at 10,000 rpm. The FITC-PBS solution (50 μl) was added to each tube of bacteria and then incubated for 1 hour at 37° C. with slight agitation. PBS (950 μl) was added to each tube and centrifuged for 2 minutes at 10,000 rpm. The pellet was washed once with 1 ml of PBS and once with 1 ml of BSA-Hanks balanced salt solution (BSA-HBBS). The FITC labelled meningococci were reconstituted in 1% BSA-HBBS and divided into 100 μl aliquots which were stored at −20° C. until use in the assay.

Human polymorphic nuclear cells (PMN) were isolated from the peripheral blood of healthy adults in heparin-containing tubes (Becton Dickinson, Mountain View, Calif.). A volume of 10 ml of blood was diluted with an equal amount of phosphate buffered saline (PBS; pH 7.4) and layered on a Ficoll histopaque gradient consisting of 10 ml of Ficoll Paque™ (Pharmacia, Uppsaila, Sweden) on top of 12 ml of histopaque (density 1.119, Sigma Diagnostics, St. Louis, Mo.). After centrifugation at 400×g for 20 minutes at room temperature, the PMN were collected from the upper part of the histopaque and ice cold RPMI medium (Roswell Park Memorial Institute, NY) containing 1% gelatin was added. Cells were centrifuged at 250×g and the residual erythrocytes were lysed by resuspending the cells in 9 ml of ice cold distilled water. After 1 minute, concentrated PBS and RPMI-gelatin was added to make the cell suspension isotonic. The PMN were centrifuged and resuspended in RPMI medium to a density of $1 \times 10^7$/ml. The purity and viability of the PMN was greater than 95%.

To a microtiter plate was added appropriate dilutions of monoclonal antibody to be tested (diluted in BSA-HBBS), 5 μl of 10% human complement (in BSA-HBBS), and 25 μl of FITC-labelled bacteria suspension to yield a total volume of 50 μl. Selected antibodies were tested without complement, and with up to three different complement sources: normal pooled human serum; agammaglobulinemic serum; and infant rabbit serum, varying the complement concentration from 1 to 10%. Each assay included a positive and negative antibody control, as well as a complement, non-opsonization and a cells-only control. The opsonization reaction was allowed to proceed for 30 minutes at 37° C. on a shaker before terminating the reaction by placing the microtiter plate on ice.

Phagocyte cell suspension (50 μl) was added to a final concentration of $5 \times 10^6$ cells/ml. This gives a ratio of bacteria to phagocytes of 10:1. Phagocytosis was allowed to proceed for 30 minutes at 37° C. on a shaker, after which time it was placed on ice. Cold BSA-HBBS (100 41) was added to each well. The plates were centrifuged for 10 minutes at 1100 rpm. Supernatants were aspirated from the wells and the cells were washed twice more with 150 μl of cold BSA-HBBS. Cold BSA-HBBS (150 μl) was then added, and the resulting cell suspensions were transferred to sterile tubes. A solution of 2% paraformaldehyde (Polysciences, Inc., Warrington, Pa.) in PBS was added to fix the cells. The samples were then analyzed by indirect florescence flow cytometry.

The results of the opsonization experiments for sixteen representative SEAM monoclonal antibodies are reported in Table 1. All antibodies found to be opsonic were also bactericidal in the assay described above using at least one of the complement sources. However, as can be seen in Table 1, there are examples of antibodies that were bactericidal but not opsonic (see, e.g., SEAM-2, SEAM-5, SEAM-7, SEAM-16, and SEAM-41).

(h) Evaluation of Autoreactivity:

Partially purified tissue culture supernatants containing the 39 SEAM monoclonal antibodies were evaluated for autoreactivity to host polysialic acid. In one assay, the monoclonal antibodies were assessed for their ability to cross-react with the human neuroblastoma cell line CHP-134 (Livingston et al. (1988) *J. Biol. Chem.* 263:9443) using flow cytometric detection of indirect immunofluorescence. In this assay, the CHP-134 cells, which express long chain polysialic acid (PSA) associated with neuronal cell adhesion molecule (NCAM) on their surface, serve as cellular markers for human PSA antigens. In control experiments, nearly confluent cell cultures were collected in 50 ml centrifuge tubes and centrifuged at 1000×g. After the supernatant was decanted, 5 ml of Blocking Buffer was added to resuspend the cells. The cells were then counted in a hemacytometer, and divided into two equal aliquots. One aliquot was incubated for 2 hours at ambient temperature with exoneuraminidase (10 units/$10^8$ cells, SIGMA Chemical Co., Saint Louis, Mo.); the other aliquot was treated identically but without enzyme. After incubation, the cells from each aliquot were distributed among individual reaction tubes so that each tube contained $10^6$ cells. To wash the cells, 2 ml of Blocking Buffer was added to each reaction tube, the tubes centrifuged at 1000 rpm in a Sorvall RT-600B for 6 minutes at 20° C., and the supernatant aspirated off. The washed cells were incubated for 2 hours in a total volume of 200 μl on ice with either no antibody, or the indicated concentration (usually 10 or 100 μg/ml) of the test antibody (i.e., SEAM MAbs).

Control antibodies in the assay included: (1) an IgG monoclonal antibody of irrelevant specificity (VIIG10, as a negative control); (2) an IgM anti-polysialic acid monoclonal antibody (2-1B, as a positive control); and (3) an anti-CD56 monoclonal antibody specific for the protein backbone of NCAM (Immunotech, Marseille, France). Blocking Buffer (2 ml) was added to each reaction tube, and the tubes were centrifuged at 1000 rpm in the Sorvall RT-600B for 6 minutes at 20° C. Following centrifugation, the supernatant was aspirated off and the cells incubated for 1 hour at ambient temperature with 150 μl of fluorescein isothiocyanate (FITC)-conjugated F(ab')$_2$ fragment goat anti-mouse IgG (H+L) (diluted to 4 μg/ml) (Jackson Immune Research, West Grove, Pa.). After washing with Blocking Buffer, 400 μl of 0.25% formaldehyde in PBS buffer (50 mM sodium phosphate, pH 7.0, 150 mM sodium chloride) was added to the cells, and the cells were analyzed by flow cytometry using a FACSCAN™ cell sorter (Becton-Dickinson, Mountain View, Calif.).

All antibodies were tested at final concentrations of 10 and 100 μg/ml of antibody in replicate, using untreated cells, and cells that had been pre-treated with neuraminidase. This treatment cleaves the surface polysialic acid and provides a control in the assay for specificity of antibody binding to polysialic acid. In a typical experiment, cells incubated without primary antibody, or with a control monoclonal antibody having an irrelevant antigenic specificity, show very little fluorescence (approximately 98% of the cells have <10 units of fluorescence). In contrast, virtually all cells treated with the anti-NAc MenB PS monoclonal antibody, 2-1B, fluoresce strongly. This fluorescence is decreased to control levels when the antibody is incubated with cells that had been pre-treated with neuraminidase. Similarly, cells treated with anti-CD56 fluoresce strongly. With this antibody, the fluorescence is unaffected by pre-treatment of the cells with neuraminidase since the CD56 determinant is located in the protein backbone of NCAM and is unaffected by the removal of polysialic acid with neuraminidase.

The SEAM-5 antibody gives no detectable binding when tested at 100 μg/ml, and is considered as negative in this assay. The SEAM-35 antibody shows strong polysialic acid-specific binding when tested at 10 or 100 μg/ml, and is considered positive. A few anti-NPr MenB PS monoclonal antibodies show binding when tested at 100 μg/ml, but appear to be negative when tested at 10 μg/ml (e.g., SEAM-12). Such antibodies are considered minimally autoreactive for the purposes of this application. A rare antibody appeared to have weak reactivity with the neuroblastoma cell line that was unaffected by the by pre-treatment of the cells with neuraminidase (e.g., SEAM-7). The autoreactivity of such antibodies with polysialic acid was scored as indeterminant in the assay, and these antibodies were also considered to have minimal autoreactivity to host PSA for purposes of this application.

Table 1 summarizes the autoantibody activity of each antibody as determined in this indirect fluorescence flow cytometry assay. Cross-reactivity with polysialic acid antigens expressed in CHP-134 cells was closely correlated with the cross-reactivity of the antibodies with NAc-MenB PS in the ELISA assay. As shown in Table 1, monoclonal antibodies that did not cross react with NAc-MenB PS in the ELISA also did not bind to CHP-134 cells, while all of the antibodies that cross-reacted with NAc-MenB PS in the ELISA also cross-reacted with PSA. This correlation between the two assays was not unexpected since the polysaccharide covalent structure of NAc-MenB PS and the host PSA is reported to be the same.

EXAMPLE 5

Identification of Molecular Mimetics of MenB Antigen Using SEAM Monoclonal Antibodies The following procedures were carried out in order to identify molecular mimetics that interact with the SEAM monoclonal antibodies of the present invention. Combinatorial synthetic molecules were synthesized according to the procedures of Zuckerman et al described above. (See Zuckermann et al. (1996) *Methods in Enzymology* 267:437, and Zuckermann et al. (1992) *J. Am. Chem. Soc.* 114:10646). Molecular mimetics were identified by fractionating tehpool by reverse-phase HPLC. The pool (~200 μl or a 10 μM/molecule solution in DMSO) was injected onto a Dynamax C18 reverse-phase column (Varian, Palo Alto, Calif.) and eluted with a alinear gradient of acetonitrile from 0% to 80% (v/v) in 0.1 % trifluoroacetic acid over a period of 60 min. The fractions were lyophilized and resuspended in 40 μl of DMSO or acetonitrile/water (1:1). Aliquots (5 μl) of each fraction were then tested by inhibiting binding of particular SEAM monoclonal antibodies to Npr-MenB PS in ELISA. Molecules in fractions having inhibitory activity were then identified by LC/MS (HP1100 LC/MSD, Hewlwtt-Packard, Palo Alto, Calif.).

SEAM monoclonal antibodies (100 μl) diluted in PBS to a concentration approximately equal to the concentration required to give an $OD_{405}$ in 30 min in the standard ELISA assay described above, were added to wells of an NPr-MenB PS-coated plate. Solutions (1–2 μl) of combinatorial synthetic molecules in DMSO were added to the monoclonal antibody solutions (final concentration of 1 μM per molecule in pool) and incubated at 4° C. overnight. Controls included wells with (1) antibody alone, (2) buffer alone, and (3) antibody and buffer, each with 1–2 μl DMSO. The plates were washed four times with PBS, and developed as described previously. Pools were screened with SEAM monoclonal antibodies SEAM-2, SEAM-3, SEAM-5, SEAM-12, SEAM-16, SEAM-18, and SEAM-28 and were judged to be positive if the inhibition compared to antibody with DMSO was ≧80% of binding observed in the absence of inhibitor.

The molecular mimetics of structure 1, as described above, were identified as inhibiting binding of particular SEAM monoclonal antibodies to NPr-MenB PS in ELISA assays. The $IC_{50}$ values (estimated concentration of the individual compound sufficient to inhibit 50% binding of SEAM monoclonal antibodies to NPr-MenB PS) were determined by serial dilution of the pools in the ELISA described above. The $IC_{50}$ concentrations of the molecular mimetics of the invention range from ~3 nM to 700 nM assuming a single active molecule in the pool.

EXAMPLE 6

Preparation of Molecular Mimetic Vaccine Compositions

Vaccine compositions containing small molecules corresponding to the above-described mimetics are prepared by non-covalent association, or covalent linkage of the mimetic to carrier proteins. Hydrophobic or reactive groups are added to the mimetic to facilitate association of the smaller mimetic molecule to a carrier protein in a manner that preserves the ability of the mimetic to inhibit SEAM monoclonal antibody binding to NPr-MenB PS in an ELISA.

Preparation of OMP Vesicles. OMP vesicles are prepared from the capsular-deficient mutant strain of *Neisseria meningitidis* Group B (Strain M7), using a combination of the techniques described by Lowell et al. (1988) *J. Expt. Med.* 167:658–663 and Zollinger et al. (1979) *J. Clin. Invest.* 63:836–848. In brief, bacteria are grown in MH broth, pelleted by centrifugation and re-suspended in 15 ml buffer containing 0.05 M Tris-HCl, 0.15 M NaCl and 0.01M EDTA (pH 7.4), and then warmed to 56° C. for 30 minutes. After cooling to room temperature, the suspension is sheared in a Polytron (Kinematica GmbH., Luzern, Switzerland) at full speed for 3 minutes and then centrifuged at 16000×g for 15 minutes. The resulting pellet is resuspended with 10 ml buffer (500 mM sodium chloride, 50 mM sodium phosphate), and treated with 5 ml of Detergent Solution (10% sodium deoxycholate (DOC) (Calbiochem, La Jolla, Calif.), 0.15 M glycine (Biorad, Hercules, Calif.) and 30 mM ethylenediaminetetraacetic acid (EDTA) (SIGMA, Saint Louis, Mo.). The suspension is centrifuged at 16,000×g for 15 minutes. The supernatant is then collected and centrifuged at 100,000×g for 2 hrs. A pellet containing the outer membrane protein preparation is resuspended in 10 ml of water and stored at 4° C.

The 10 ml suspension of outer membrane protein is retreated with 5 ml of the Detergent Solution, and then wanned to 56° C. for 30 minutes. After cooling, lipopolysaccharide (LPS) is removed from the outer membrane protein by chromatography, 2 ml at a time, using a 2 cm×20 cm Sephadex G-100 column (Pharmacia Fine Chemicals, Piscataway, N.J.) in a second detergent solution (1% DOC, 0.05 M glycine, and 0.005 M EDTA, pH 8.8). The peak fractions are collected, warmed to 30° C. and sterile-filtered through a 0.2 μm membrane filter directly into 4 volumes of cold, filter-sterilized ethanol. This mixture is incubated at 4° C. overnight. The resulting precipitate is collected by centrifugation at 16,000×g for 10 minutes, and resuspended in 1 ml of sterile distilled water. The resulting OMP preparation is stored at −60° C.

A molecular mimetic containing a Lauroyl-GLY-GLY group is complexed to OMP vesicles via hydrophobic interactions by combining equal amounts by weight of the Lauroyl-GLY-GLY derivative and OMP vesicles solubilized in detergent solution (1% DOC, 0.05 M glycine, and 0.005 M EDTA). The solution is placed in a dialysis tube with a molecular weight cut-off of 10,000 Daltons and dialyzed against 3L of phosphate buffered saline (PBS, 50 mM sodium phosphate, pH 7.0, 150 mM NaCl) in three buffer changes of 1L each over a period of 24 hours.

Preparation of Molecular Mimetic-Carrier Protein Conjugates. Keyhole Limpet Hemocyanin (KLH, e.g., Imject®, Pierce, Rockford, Ill.) is resuspended in 2 ml of distilled water to give a final concentration of 10 mg/ml. 200 µl of this solution is added to a 1.5 ml microcentrifuge tube. A heterobifunctional cross-linking reagent (2 mg) containing an N-hydroxysuccinimide active ester and a maleimide group such as Sulfo-SMCC® (Pierce, Rockford, Ill.) is dissolved in 1 ml of Conjugation Buffer (0.083 M sodium phosphate, 0.9 M sodium chloride, 0.1 M EDTA, pH 7.2). 100 µl of the Sulfo-SMCC solution is immediately combined with the KLH solution and allowed to react for 1 hour at ambient temperature. The solution is applied to a 1.5 cm×10 cm column of Sephadex G-25 equilibrated with Conjugation Buffer. The maleimide-activated KLH eluting in the void volume is collected and retained. A molecule mimetic, as described above, containing a cysteine amino acid is resuspended in 100 µl of DMSO and added to the solution of maleimide-activated KLH. The mixture is allowed to react at ambient temperature for 18 hours. The reaction is terminated by adding β-mercapto ethanol to a final concentration of 5 mM. Finally, the hapten-carrier conjugate is purified by gel permeation chromatography on a 2 cm×25 cm column of Sephadex G-25 equilibrated with PBS. The column is monitored by UV absorbance at 280 nm.

EXAMPLE 7

Inhibition of Antibody Binding to NPr-MeB PS by Small Molecule Mimetics of NPr-MenB PS epitopes Small molecule mimetics of NPr-MenB PS epitopes (Structures 5A(1), 5B(1), 6A(1) and 6B(2)) were synthesized as described above. The molecular mimetics have the following structures:

A competitive solid phage ELISA procedure was used to assess the ability of small molecule mimetics of NPr-MenB PS epitopes to inhibit binding of the monoclonal antibody molecules to solid phase NPr-MenB PS. The assay was performed as described above for the Inhibition of Antibody to NPr-MenB PS by Oligomers ELISA, with the exception that the monoclonal antibodies were pre-diluted to concentrations to yield and OD of 0.5 to 1 in PBS. The monoclonal antibodies were then added to wells of replica plates, each containing 70 μl of PBS and 5 μl of inhibitor diluted in acetonitrile/water (1:1), which was added prior to adding 50 μl of the antibody solution. The inhibitor and antibody were incubated with the NPr-MenB PS ELISA plate at ambient temperature for 1 hr. The results for inhibition by four molecular mimetics of four SEAM antibodies is shown graphically in FIGS. 1A–1D. Particularly, FIG. 1 illustrates the concentration-dependent inhibition of (A) SEAM 3 (10 mg/ml); (B) SEAM 7 (10 mg/ml); (C) SEAM 18 (10 mg/ml); and (D) SEAM 30 (10 mg/ml) by structure 5A(1), 5B(1), 6A(1) and 6B(1).

(a) Cross-Reactivity with Molecular Minmetics Coated Directly on ELISA Plates

The monoclonal antibodies were evaluated for their ability to cross-react with the molecular mimetics as demonstrated by direct binding to the molecular mimetics in a solid phase ELISA format. The method used was similar to that described above for the NPr-MenB PS ELISA, with the following exceptions. The antibodies were diluted in PBS and the plates were incubated at ambient temperature for 1 hr. The plates were washed five times with PBS, and the alkaline phosphatase conjugated anti-murine IgG, IgM, and IgA polyclonal antibodies (Zymed) were diluted in PBS and incubated at ambient temperature on the ELISA plates. FIG. 2 depicts the binding of SEAM 3 (10 mg/ml), SEAM 7 (10 mg/ml), SEAM 18 (10 mg/ml) and SEAM 30 (10 mg/ml) to structures 5A(1), 5B(1), 6A(1) and 6B(1).

EXAMPLE 8

Preparation of Bovine Serum Albumin Conjugates of Structures 5A(1),5B(1), 6A(1) and 6B(2)

A solution of structure 5A(1), 5B(1), 6A(1) or 6B(2) (150 μl, ~50 mM) in dimethyl sulfoxide was combined with 50 μl of 0.17 M MBS (Pierce Chemical Co., Rockford, Ill.) in dimethyl sulfoxide. Approximately 20 μl of 1 M Hepes buffer (Sigma), pH 8.0 was added to neutralize acid released from the reaction. After 1 hr incubation at ambient temperature, 0.5 ml of 10 mg/ml BSA (Imject, Pierce) was added. After incubation for 18 hrs at ambient temperature, the mixture was purified by passing it through a 10-DG gel filtration column (Bio-Rad, Richmond, Calif.) equilibrated with PBS. Fractions (0.5 ml) were collected and tested for the presence of protein using a BCA protein assay (Pierce). The first three fractions eluting from the column that contained protein were combined.

(a) Cross-reactivity of SEAM Antibodies with BSA Conjugates of Structures 5A(1),5B(1), 6A(1) and 6B(2)

The BSA conjugates of Structures 5A(1),5B(1), 6A(1) and 6B(2) were diluted 1:1000 in PBS and 100 μl of each was added to wells of microtiter plates (Immulon 2, available from Dynatech Laboratories, Inc.). The plates were incubated overnight at 4° C. The wells were washed three times with PBS, filled with 250 μl of Blocking Buffer and incubated for 30 to 60 minutes at ambient temperature to block nonspecific binding sites. Then the plates were washed three times with Washing Buffer. Antibodies to be tested were diluted in PBS and then added 100 μl per each well. The plates were covered and incubated overnight at 4° C.

After incubation overnight, the wells were washed five times with PBS and incubated for 1 hour at ambient temperature with 100 μl/well of alkaline phosphatase conjugated anti-murine IgG, IgM, and IgA polyclonal antibodies (Zymed) that were diluted 1:2000 in PBS. The plates were then washed with PBS, and 100 μl of freshly prepared substrate (p-Nitrophenyl phosphate, Sigma) diluted to 1 mg/ml in Substrate Buffer was added to each well. Absorbance values at 405 nm were measured after approximately 30 minutes. FIG. 3 depicts the binding of SEAM 3 (10 mg/ml), SEAM 7 (10 mg/ml), SEAM 18 (10 mg/ml) and SEAM 30 (10 mg/ml) to structures 5A(1), 5B(1), 6A(1) and 6B(1) described above.

Thus, novel molecular mimetics of unique epitopes of MenB, and methods for obtaining and using the same are disclosed. Although preferred embodiments of the subject invention have been described in some detail, it is understood that obvious variations can be made without departing from the spirit and the scope of the invention as defined by the appended claims.

Deposits of Strains Useful in Practicing the Invention

Deposits of biologically pure cultures of the following hybridoma cell lines were made with the American Type Culture Collection (ATCC), 12301 Parklawn Drive, Rockville, Md. The accession numbers indicated were assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, and subject to an agreement between Chiron Corporation and the ATCC, which assures permanent and unrestricted availability of the progeny to one determined by the U.S. Commissioner of Patents and Trademarks to be entitled thereto according to 35 U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these hybridomas, as well as the amino acid sequences of the antibody molecules encoded thereby, are incorporated herein by reference and are controlling in the event of any conflict with the description herein. A license may be required to make, use, or sell the deposited materials, and no such license is hereby granted.

| HYBRIDOMA | Deposit Date | ATCC No. |
|---|---|---|
| SEAM-3 | August 16, 1996 | HB-12170 |
| SEAM-18 | August 16, 1996 | HB-12169 |
| SEAM-2 | July 30, 1997 | CRL-12380 |
| SEAM-12 | July 30, 1997 | CRL-12381 |

We claim:

1. A molecular mimetic of a unique epitope of *Neisseria meningitidis* serogroup B (MenB) having the following structure 1:

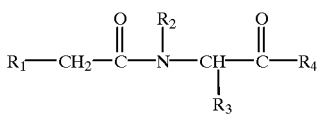 (1)

wherein:

$R_1$ is —$NR_5R_6$;

$R_2$ is —$(CH_2)_p$—$R_{11}$, wherein p is an integer from 0–8;

$R_3$ is H, 1–6C alkyl, aryl, alkyl-aryl, 2–6C alkenyl, or 2–6C alkynyl;

$R_4$ is —$NH_2$, —NHOH, —$NHNH_2$, —OH, —SH, or a multivalent linker moiety selected from the group of amines consisting of amino acids, peptoids, peptides, and —$NH(CH_2)_qSH$, wherein q is an integer from 1–5;

$R_5$ is $R_2$, H or $R_5$ and $R_6$ taken together form a carbocyclic or aryl ring, said ring optionally containing up to two heteroatoms selected from the group consisting of consisting of N, O and S;

$R_6$ is —CO—$(CH_2)_m$—$R_7$, wherein m is an integer from 1–6;

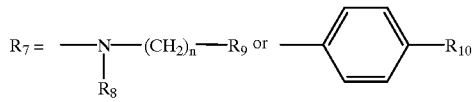

wherein n is an integer from 0–5;

$R_8$ is H, 1–3C alkyl or acyl;

$R_9$ is —$NH_2$, —NH—$NH_2$, —$CONH_2$, acyl, —COOH, —SH, —S-alkyl, —S-aryl, sulfonic acid or sulfonamide, with the proviso that when n=0, $R_9$ is not —NH—$NH_2$;

$R_{10}$ is H, 1–6C alkyl, halogen, OH, 1–6C alkoxy, acyl, amino, 1–5C alkylamino, amide, —COOH, —SH, —S-alkyl, —S-aryl, sulfonic acid or sulfonamide; and $R_{11}$ is a carbocyclic ring or an aryl ring which is optionally substituted, —CH=CH—$(CH_2)_p$—$CH_3$, —$CF_3$, —OH, 1–6C alkoxy, acyl, amino, —N$(CH_3)_2$, —NH—$NH_2$, amide, —COOH, —SH, —S-alkyl, —S-aryl, sulfonic acid or sulfonamide;

with the proviso that when $R_3$ is H; $R_4$ is —$NH_2$; and p is 0 or 1; $R_5$ and $R_6$ taken together do not form a bicyclic substituted carbocyclic or aryl ring, wherein one of the rings is a 7-membered ring.

2. The molecular mimetic of claim 1 having the following structure:

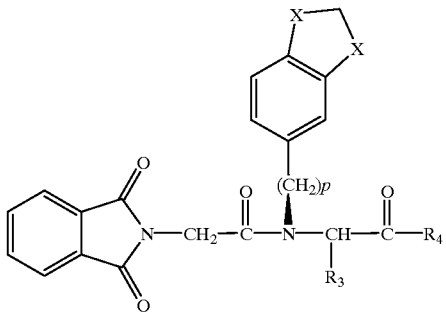 (2)

wherein X is O, N, S or $CH_2$; $R_3$ is H or alkyl; $R_4$ is —$NH_2$, —NHOH, —$NHNH_2$, —OH or —SH and p=0–3.

3. The molecular mimetic of claim 1 having the following structure:

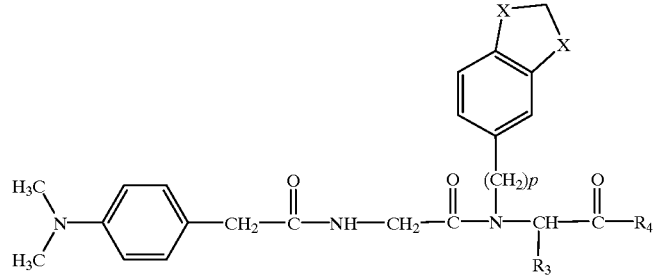 (3)

wherein X is O, N, S or $CH_2$; $R_3$ is H or alkyl; $R_4$ is —$NH_2$, —NHOH, —$NHNH_2$, —OH or —SH and p=0–3.

4. The molecular mimetic of claim 1 having the following structure:

(4)

[Structure 4: H₃C-C(=O)-[benzene]-C(=O)-NH-CH₂-C(=O)-N-CH(R₃)-C(=O)-R₄, with (CH₂)p linker to benzo-fused ring with two X atoms]

wherein X is O, N, S or CH₂; R₃ is H or alkyl; R₄ is —NH₂, —NHOH, —NHNH₂, —OH or —SH; and p=0–3.

5. The molecular mimetic of claim 1 having a structure selected from the group consisting of the following structures:

(5A)

[Structure 5A]

and (5B)

[Structure 5B]

wherein X is O, N, S or CH₂; R₃ is H or alkyl; R₄ is —NH₂, —NHOH, —NHNH₂, —OH or —SH; p=0–3; R₈ is H or COCH₃; and R₉ is —COOH, —NH₂, —NHNH or

[—S—CH₂—(2-Cl, 6-F phenyl)]

6. The molecular mimetic of claim 1 having a structure selected from the group consisting of the following structures:

(6A)

[Structure 6A]

and (6B)

[Structure 6B]

wherein X is O, N, S or CH₂; R₃ is H or alkyl; R₄ is —NH₂, —NHOH, —NHNH₂, —OH or —SH; p=0–3; R₈ is H or COCH₃; and R₉ is —COOH, —NH₂, —NHNH₂ or

[—S—CH₂—(2-Cl, 6-F phenyl)]

7. A composition comprising a molecular mimetic of a unique epitope of *Neisseria meningitidis* serogroup B (MenB), in combination with a pharmaceutically acceptable excipient, having the following structure:

(1)

R₁—CH₂—C(=O)—N(R₂)—CH(R₃)—C(=O)—R₄ wherein:

$R_1$ is —$NR_5R_6$;

$R_2$ is —$(CH_2)_p$—$R_{11}$, wherein p is an integer from 0–8;

$R_3$ is H, 1–6C alkyl, aryl, alkyl-aryl, 2–6C alkenyl, or 2–6C alkynyl;

$R_4$ is —$NH_2$, —NHOH, —$NHNH_2$, —OH, —SH, or a multivalent linker moiety selected from the group of amines consisting of amino acids, peptoids, peptides, and —$NH(CH_2)_qSH$, wherein q is an integer from 1–5;

$R_5$ is $R_2$, H or $R_5$ and $R_6$ taken together form a carbocyclic or aryl ring, said ring optionally containing up to two heteroatoms selected from the group consisting of N, O and S;

$R_6$ is —CO—$(CH_2)_m$—$R_7$, wherein m is an integer from 1–6;

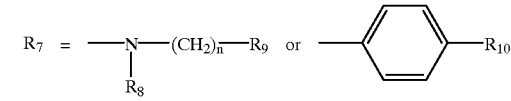

wherein n is an integer from 0–5;

$R_8$ is H, 1–3C alkyl or acyl;

$R_9$ is —$NH_2$, —NH—$NH_2$, —$CONH_2$, acyl, —COOH, —SH, —S-alkyl, —S-aryl, sulfonic acid or sulfonamide, with the proviso that when n=0, $R_9$ is not —NH—$NH_2$;

$R_{10}$ is H, 1–6C alkyl, halogen, OH, 1–6C alkoxy, acyl, amino, 1–5C alkylamino, amide, —COOH, —SH, —S-alkyl, —S-aryl, sulfonic acid or sulfonamide; and $R_{11}$ is a carbocyclic ring or an aryl ring which is optionally substituted, —CH=CH—$(CH_2)_p$—$CH_3$, —$CF_3$, —OH, 1–6C alkoxy, acyl, amino, —N$(CH_3)_2$, —NH—$NH_2$, amide, —COOH, —SH, —S-alkyl, —S-aryl, sulfonic acid or sulfonamide.

8. The composition of claim 7 wherein said molecular mimetic has the following structure:

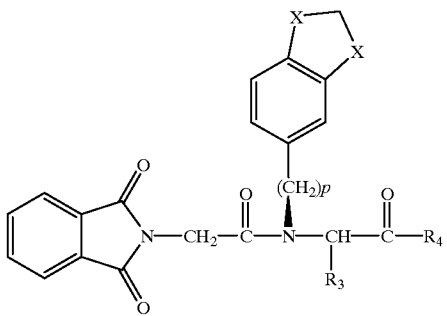

(2)

wherein X is O, N, S or $CH_2$; $R_3$ is H or alkyl; $R_4$ is —$NH_2$, —NHOH, —$NHNH_2$, —OH or —SH and p=0–3.

9. The composition of claim 7 wherein said molecular mimetic has the following structure:

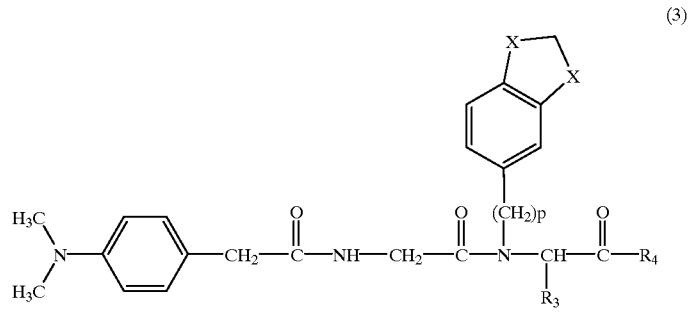

(3)

wherein X is O, N, S or $CH_2$; $R_3$ is H or alkyl; $R_4$ is —$NH_2$, —NHOH, —$NHNH_2$, —OH or —SH and p=0–3.

10. The composition of claim 7 wherein said molecular mimetic has the following structure:

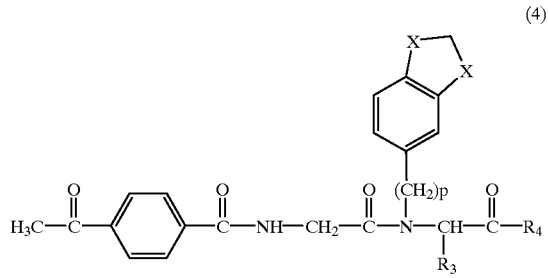

(4)

wherein X is O, N, S or $CH_2$; $R_3$ is H or alkyl; $R_4$ is —$NH_2$, —NHOH, —$NHNH_2$, —OH or —SH and p=0–3.

11. The composition of claim 7 wherein said molecular mimetic has a structure selected from the group consisting of the following structures:

(5A)

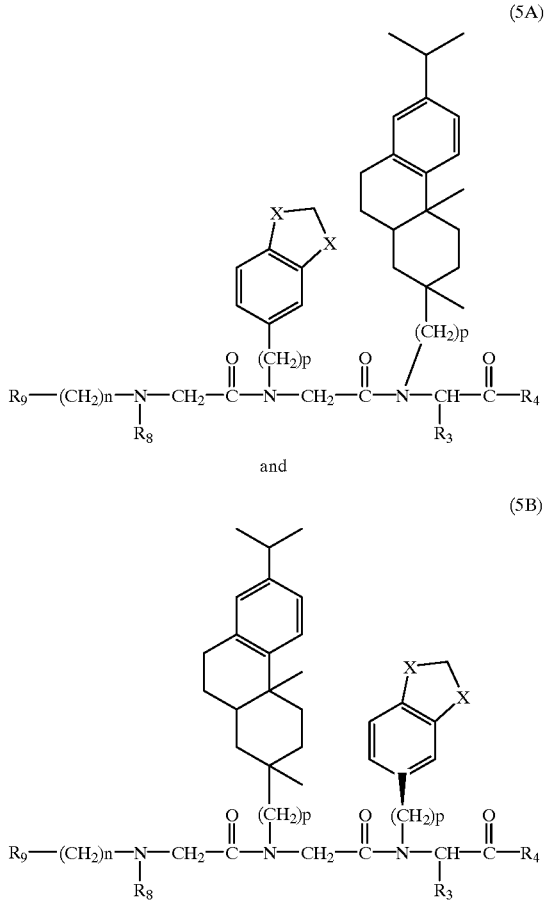

and (5B)

wherein X is O, N, S or CH$_2$; R$_3$ is H or alkyl; R$_4$ is —NH$_2$, —NHOH, —NHNH$_2$, —OH or —SH; p=0–3; R$_8$ is H or COCH$_3$; and R$_9$ is —COOH, —NH$_2$, —NHNH$_2$ or

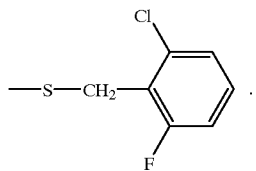

12. The composition of claim 7 wherein said molecular mimetic has a structure selected from the group consisting of the following structures:

(6A)

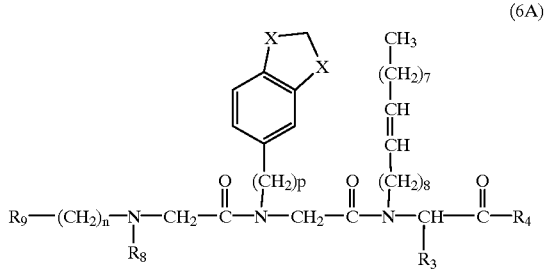

and (6B)

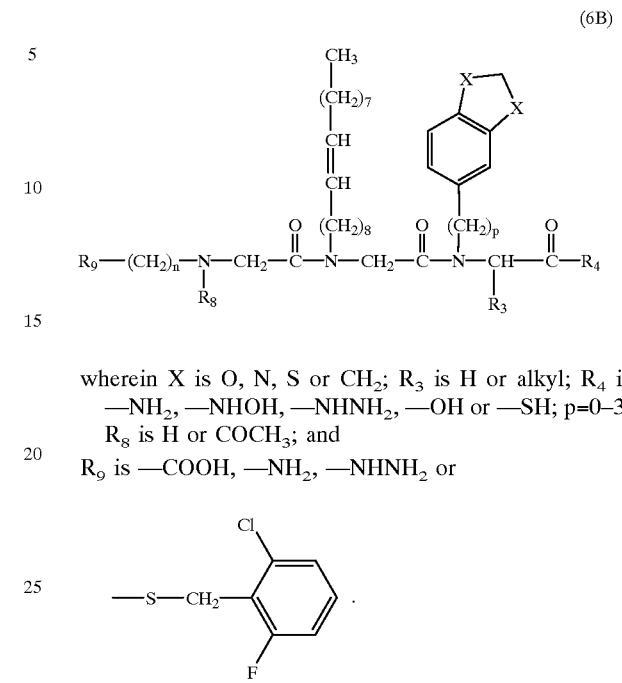

wherein X is O, N, S or CH$_2$; R$_3$ is H or alkyl; R$_4$ is —NH$_2$, —NHOH, —NHNH$_2$, —OH or —SH; p=0–3; R$_8$ is H or COCH$_3$; and R$_9$ is —COOH, —NH$_2$, —NHNH$_2$ or 13. The composition of claim 7, wherein said molecular mimetic is covalently bound to a carrier molecule.

14. The composition of claim 7, wherein said molecular mimetic is non-covalently associated with a carrier molecule.

15. The composition of claim 7 further comprising an immunological adjuvant.

16. A method for preventing *Neisseria meningitidis* serogroup B and/or *E. coli* K1 disease in a mammalian subject, said method comprising administering an effective amount of the composition of claim 7 to said subject.

17. A method for preventing *Neisseria meningitidis* serogroup B and/or *E. coli* K1 disease in a mammalian subject, said method comprising administering an effective amount of the composition of claim 15 to said subject.

18. A method for detecting *Neisseria meningitidis* serogroup B and/or *E. coli* K1 antibodies in a biological sample comprising:
  (a) providing a biological sample;
  (b) reacting said biological sample with a molecular mimetic according to claim 1 under conditions which allow *Neisseria meningitidis* serogroup B and/or *E. coli* K1 antibodies, when present in the biological sample, to bind to said molecular mimetic to form an antibody/mimetic complex; and
  (c) detecting the presence or absence of said complex thereby detecting the presence or absence of *Neisseria meningitidis* serogroup B and/or *E. coli* K1 antibodies in said sample.

19. An immunodiagnostic test kit for detecting *Neisseria meningitidis* serogroup B and/or *E. coli* K1 infection, said test kit comprising a molecular mimetic according to claim 1 and instructions for conducting the immunodiagnostic test.

* * * * *